US009637531B2

(12) United States Patent
Lee et al.

(10) Patent No.: US 9,637,531 B2
(45) Date of Patent: May 2, 2017

(54) SELECTIVE CARTILAGE THERAPY

(71) Applicant: The Brigham and Women's Hospital, Inc., Boston, MA (US)

(72) Inventors: Richard T. Lee, Weston, MA (US);
Parth Patwari, Cambridge, MA (US);
Francesco Loffredo, Boston, MA (US);
James Pancoast, Cambridge, MA (US);
Zheng Xin Dong, Holliston, MA (US);
Todd Vannelli, Milford, MA (US)

(73) Assignee: The Brigham and Women's Hospital, Inc, Boston, MA (US)

( * ) Notice: Subject to any disclaimer, the term of this patent is extended or adjusted under 35 U.S.C. 154(b) by 84 days.

(21) Appl. No.: 14/409,312

(22) PCT Filed: Jun. 25, 2013

(86) PCT No.: PCT/US2013/047556
§ 371 (c)(1),
(2) Date: Dec. 18, 2014

(87) PCT Pub. No.: WO2014/004467
PCT Pub. Date: Jan. 3, 2014

(65) Prior Publication Data
US 2015/0166628 A1 Jun. 18, 2015

Related U.S. Application Data

(60) Provisional application No. 61/663,686, filed on Jun. 25, 2012, provisional application No. 61/750,999, filed on Jan. 10, 2013.

(51) Int. Cl.
C07K 14/65 (2006.01)
C07K 7/00 (2006.01)
C07K 14/475 (2006.01)
A61K 38/30 (2006.01)
C07K 14/47 (2006.01)

(52) U.S. Cl.
CPC ............ *C07K 14/65* (2013.01); *A61K 38/30* (2013.01); *C07K 14/47* (2013.01); *C07K 14/475* (2013.01); *C07K 2319/00* (2013.01)

(58) Field of Classification Search
None
See application file for complete search history.

(56) References Cited

U.S. PATENT DOCUMENTS

| 5,652,214 A | 7/1997 | Lewis et al. |
| 5,670,483 A | 9/1997 | Zhang et al. |
| 5,786,217 A | 7/1998 | Tubo et al. |
| 6,037,329 A | 3/2000 | Baird et al. |
| 6,150,163 A | 11/2000 | McPherson et al. |
| 6,548,630 B1 | 4/2003 | Zhang et al. |
| 7,399,831 B2 | 7/2008 | Lee et al. |
| 7,429,567 B2 | 9/2008 | Lee et al. |
| 2004/0087505 A1 | 5/2004 | Pena et al. |
| 2005/0222394 A1 | 10/2005 | Zamora et al. |
| 2006/0088510 A1 | 4/2006 | Lee et al. |
| 2006/0148703 A1 | 7/2006 | Lee et al. |
| 2006/0172931 A1 | 8/2006 | San Antonio et al. |
| 2008/0138323 A1 | 6/2008 | Lee |
| 2009/0143566 A1 | 6/2009 | Zamora et al. |
| 2010/0215731 A1 | 8/2010 | Emans et al. |

FOREIGN PATENT DOCUMENTS

| WO | 99/54359 | 10/1999 |
| WO | 2004/018499 A2 | 3/2004 |
| WO | WO 2011/073199 | * 6/2011 |
| WO | WO 2011/073199 A1 | * 6/2011 |

OTHER PUBLICATIONS

Ngo et al. Computational Complexity, Protein Structure Prediction and the Levinthal Paradox. The Protein Folding Problem and Tertiary Structure Prediction, pp. 433-440 and 492-495 (1994).*
Tokuriki et al. Stability effects of mutations and protein evolvability, Current Opinion in Structural Biology, 19:596-604 (2009).*
Wells, J.A. Additivity of Mutational Effects in Proteins. Biochemistry 29:8509-8517 (1990).*
Abraham et al., Biochemical and Biophysical Research Communications 190(1):125-133 (1993). "Heparin-binding EGF-like growth factor: characterization of rat and mouse cDNA clones, protein domain conservation across species, and transcript expression in tissues."
Ballard et al., Biochem J. Jan. 1, 1986;233(1)223-30. Binding properties and biological potencies of insulin-like growth factors in L6 myoblasts.
Brittberg et al., The new England Journal of Medicine 331(14):879-895 (1994). "Treatment of dep cartilage defects in the knee with autologous chondrocyte transplantation."
Chevalier et al., "Production of Binding Proteins and Role of the Insulin-Like Growth Factor I Binding Protein 3 in Human Articular Cartilage Explants," British J. Rheumatol. 35:515-522 (1996).
Congote et al. "Increased heparin binding by site directed mutagenesis of a recombinant chimera of bombyxin and insulin-like growth factor II," Biochimica et Biophysica Acta 1243:538-542 (1995).

(Continued)

*Primary Examiner* — Elizabeth C Kemmerer
*Assistant Examiner* — Regina M Deberry
(74) *Attorney, Agent, or Firm* — Brown Rudnick LLP; Thomas C. Meyers

(57) ABSTRACT

The present invention relates to compositions, methods and kits for delivery of an IGF-1 protein or a functional fragment or variant, derivative thereof to cells or tissues that express proteoglycans. More specifically, the present invention relates to fusion proteins comprising a heparin binding protein (HB) comprising SEQ ID NO: 1 or SEQ ID NO: 2. Other aspects relate to use of a HB-IGF-1 fusion proteins in methods to deliver IGF-1 to the cartilage for the treatment of a cartilage related disease and disorder in a subject.

3 Claims, 4 Drawing Sheets

(56) References Cited

OTHER PUBLICATIONS

Davis et al., "Local myocardial insulin-like growth factor 1 (IGF-1) delivery with biotinylated peptide nanofibers improves cell therapy for myocardial infarction," PNAS 103(21):8155-8160 (May 2006).
De Ceuninck et al., Arthritis Rheum. Aug. 2003;48(8):2197-206. "High binding capacity of cyclophilin B to chondrocyte heparan sulfate proteoglycans and its release from the cell surface by matrix metalloproteinases: possible role as a proinflammatory mediator in arthritis."
Kofidis et al., "Insulin-Like Growth Factor Promotes Engraftment, Differentiation, and Functional Improvement after Transfer of Embryonic Stem Cells for Myocardial Restoration," Stem Cells 22:1239-1245 (2004).
Li et al., "Overexpression of Insulin-like Growth Factor-1 in Mice Protects from Myocyte Death after Infarction, Attenuating Ventricular Dilation, Wall Stress, and Cardiac Hypertrophy," J. Clin. Invest. 100:1991-1999 (Oct. 1997).
Özdinler et al., "IGF-I Specifically Enhances Axon Outgrowth of Corticospinal Motor Neurons," Nature Neurosci. 9:1371-1381 (Nov. 2006).
Palmen et al., "Cardiac Remodeling after Myocardial Infarction is Impaired in IGF-1 Deficient Mice," Cardiovasc. Res. 50:516-524 (2001).
International Preliminary Report on Patentability for PCT/US2007/023527 filed Nov. 8, 2007. (Mailed May 19, 2009.).
International Search Report for PCT/US07/23527 filed Nov. 8, 2007. (Mailed Jun. 19, 2008.).
Written Opinion of the International Searching Authority for PCT/US07/23527 filed Nov. 8, 2007. (Mailed Jun. 19, 2008.).
Schmidt et al., "A review of the effects of insulin-like growth factor and platelet derived growth factor on in vivo cartilage healing and repair," OsteoArthritis and Cartilage 14:403-412 (2006).
Search Report prepared by the Hungarian Patent Office for Singapore Application No. 2009031444. (Mailed Jun. 10, 2012.).
Segev et al., "The role of perlecan in arterial injury and angiogenesis," Cardiovascular Res. 63:603-610 (2004).
Supplementary European Search Report for Application No. EP 07 86 7389. (Mailed Oct. 29, 2009.).
Thompson et al., "Characterization of Sequences within Heparin-binding EGF-like Growth Factor That Mediate Interaction with Heparin," J. Biol. Chem. 269(4):2541-2549 (Jan. 1994).
Tokunou et al., "Abstract 1269: Engineering a New Insulin-Like Growth Factor-1 Protein for Embryonic Stem Cell Therapy," Circulation 114(18 Suppl. S):239 (2006).
Tokunou et al., FASEB J. 22(6):1886-1893 (2008). "Engineering insulin-like growth factor-1 for local delivery."
Torella et al., "Cardiac Stem Cell and Myocyte Aging, Heart Failure, and Insulin-Like Growth Factor-1 Overexpression," Circ. Res. 94:514-524 (2004).
Vasan et al., "Serum Insulin-like Growth Factor I and Risk for Heart Failure in Elderly Individuals Without a Previous Myocardial Infarction: The Framingham Heart Study," Ann. Intern. Med. 139:642-648 (2003).
Vig, et al., "Intranasal administration of IGF-I improves behavior and Purkinje cell pathology in SCA1 mice," Brain Research Bulletin 69:573-579 (2006).
Vincent et al., "Basic FGF mediates an immediate response of articular cartilage to mechanical injury," PNAS 99(12):8259-8264 (2002).
Wilczak et al., "Insulin-Like Growth Factor System in Amyotrophic lateral Sclerosis," Endocr. Dev. 9:160-169 (2005).
Written Opinion prepared by the Hungarian Patent Office for Singapore Application No. 2009031444. (Mailed Jun. 10, 2010.).
Zhang et al., "Spontaneous Assembly of a Self-Complementary Oligopeptide to Form a Stable Macroscopic Membrane," Proc. Natl. Acad. Sci. USA 90:3334-3338 (Apr. 1993).
Zhang et al., "Design of Nanostructured Biological Materials Through Self-Assembly of Peptides and Proteins," Curr. Opin. Chem. Biol. 6:865-871 (2002).
Kirn-Safran et al., Birth Defect Research (Part C) 72:69-68 (2004). "Heparan sulfate proteoglycans: coordinator of multiple signaling during chondrogenesis."
Tokunout et al., The FASEB J., 22(6):1886-1893 (2008). "Engineering insulin-like growth factor-1 for local delivery."
Veronique Hospital et al. Biochem Journal 367:229-238 (2002). "The metalloendopeptidase nardilysin (NRDc) is potently inhibited by heparin-binding epidermal growth factor-like growth factor (HB-EGF)."

* cited by examiner

```
                           SEQUENCE LISTING

<160> NUMBER OF SEQ ID NOS: 35

<210> SEQ ID NO 1
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Lys Arg Lys Lys Lys Gly Lys Gly Leu Gly Lys Lys Arg Asp Pro
1               5                   10                  15

Ser Leu Arg Lys Tyr Lys
            20

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Arg Lys Lys Lys Gly Lys Gly Leu Gly Lys Lys Arg Asp Pro Ser
1               5                   10                  15

Leu Arg Lys Tyr Lys
            20

<210> SEQ ID NO 3
<211> LENGTH: 70
<212> TYPE: PRT
<213> ORGANISM: Rattus sp.

<400> SEQUENCE: 3

Gly Pro Glu Thr Leu Cys Gly Ala Glu Leu Val Asp Ala Leu Gln Phe
1               5                   10                  15

Val Cys Gly Pro Arg Gly Phe Tyr Phe Asn Lys Pro Thr Gly Tyr Gly
            20                  25                  30

Ser Ser Ile Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Thr Lys Ser Ala
65                  70

<210> SEQ ID NO 4
<211> LENGTH: 98
<212> TYPE: PRT
```

<213> ORGANISM: Homo sapiens

<400> SEQUENCE: 4

```
Gly Pro Glu Thr Leu Cys Gly Ala Glu Leu Val Asp Ala Leu Gln Phe
1               5                   10                  15
Val Cys Gly Asp Arg Gly Phe Tyr Phe Asn Lys Pro Thr Gly Tyr Gly
            20                  25                  30
Ser Ser Ser Arg Arg Ala Pro Gln Thr Gly Ile Val Asp Glu Cys Cys
        35                  40                  45
Phe Arg Ser Cys Asp Leu Arg Arg Leu Glu Met Tyr Cys Ala Pro Leu
    50                  55                  60
Lys Pro Ala Lys Ser Ala Arg Ser Val Arg Ala Gln Arg His Thr Asp
65                  70                  75                  80
Met Pro Lys Thr Gln Lys Glu Val His Leu Lys Asn Ala Ser Arg Gly
                85                  90                  95
Ser Ala
```

<210> SEQ ID NO 5
<211> LENGTH: 70
<212> TYPE: PRT
<213> ORGANISM: Homo sapiens

<400> SEQUENCE: 5

```
Gly Pro Glu Thr Leu Cys Gly Ala Glu Leu Val Asp Ala Leu Gln Phe
1               5                   10                  15
Val Cys Gly Asp Arg Gly Phe Tyr Phe Asn Lys Pro Thr Gly Tyr Gly
            20                  25                  30
Ser Ser Ser Arg Arg Ala Pro Gln Thr Gly Ile Val Asp Glu Cys Cys
        35                  40                  45
Phe Arg Ser Cys Asp Leu Arg Arg Leu Glu Met Tyr Cys Ala Pro Leu
    50                  55                  60
Lys Pro Ala Lys Ser Ala
65                  70
```

<210> SEQ ID NO 6
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Glu Gly Pro Glu Thr Leu Cys Gly Ala Glu Leu Val Asp Ala Leu
1               5                   10                  15
Gln Phe Val Cys Gly Asp Arg Gly Phe Tyr Phe Asn Lys Pro Thr Gly
            20                  25                  30
Tyr Gly Ser Ser Ser Arg Arg Ala Pro Gln Thr Gly Ile Val Asp Glu
        35                  40                  45
Cys Cys Phe Arg Ser Cys Asp Leu Arg Arg Leu Glu Met Tyr Cys Ala
    50                  55                  60
Pro Leu Lys Pro Ala Lys Ser Ala
65                  70
```

<210> SEQ ID NO 7
<211> LENGTH: 67
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 7

```
Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala
65
```

<210> SEQ ID NO 8
<211> LENGTH: 279
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8

```
atgaaaaaga agaggaaagg caagggggtta ggaaagaaga gagatccatg ccttaagaaa      60
tacaagggac cagagaccct tgcggggct gagctggtgg acgctcttca attcgtgtgt      120
ggaccaaggg gcttttactt caacaagccc acaggctatg gctccagcat tcggagggca      180
ccacagacgg gcattgtgga tgagtgttgc ttccggagct gtgatctgag gaggctggag      240
atgtactgtg ctccgctgaa gcctacaaag tcagcttag                             279
```

<210> SEQ ID NO 9
<211> LENGTH: 92
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

```
Met Lys Lys Arg Lys Gly Lys Gly Leu Gly Lys Lys Arg Asp Pro
1               5                   10                  15

Cys Leu Lys Lys Tyr Lys Gly Pro Glu Thr Leu Cys Gly Ala Glu Leu
            20                  25                  30

Val Asp Ala Leu Gln Phe Val Cys Gly Pro Arg Gly Phe Tyr Phe Asn
        35                  40                  45

Lys Pro Thr Gly Tyr Gly Ser Ser Ile Arg Arg Ala Pro Gln Thr Gly
    50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Thr Lys Ser Ala
                85                  90
```

<210> SEQ ID NO 10
<211> LENGTH: 282
<212> TYPE: DNA
<213> ORGANISM: Artificial Sequence
<220> FEATURE:
<223> OTHER INFORMATION: Description of Artificial Sequence: Synthetic
polynucleotide -continued

```
<400> SEQUENCE: 10
atgaagcgta agaaaaaagg caaaggtctg ggcaaaaaac gtgatccgtg cctgcgcaaa      60
tataaaggtc cggaaaccct gtgcggcgca gaactggtgg atgcgctgca gtttgtttgt    120
ggtgatcgtg gcttttattt caacaaaccg accggttacg gtagctctag tcgtcgcgca    180
ccgcagacgg gtattgtgga tgaatgctgt ttccgcagct gcgatctgcg tcgcctggaa    240
atgtactgtg cgccgctgaa accggcgaaa tctgcctaat aa                        282
```

<210> SEQ ID NO 11
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 11

Met Lys Arg Lys Lys Gly Lys Gly Leu Gly Lys Lys Arg Asp Pro
1               5                   10                  15

Cys Leu Arg Lys Tyr Lys Gly Pro Glu Thr Leu Cys Gly Ala Glu Leu
                20                  25                  30

Val Asp Ala Leu Gln Phe Val Cys Gly Asp Arg Gly Phe Tyr Phe Asn
            35                  40                  45

Lys Pro Thr Gly Tyr Gly Ser Ser Ser Arg Arg Ala Pro Gln Thr Gly
        50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Ala Lys Ser Ala
                85                  90
```

<210> SEQ ID NO 12
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 12
atgaagcgta agaaaaaagg caaaggtctg ggcaaaaaac gtgatccgag cctgcgcaaa      60
tataaaggtc cggaaaccct gtgcggcgca gaactggtgg atgcgctgca gtttgtttgt    120
ggtgatcgtg gcttttattt caacaaaccg accggttacg gtagctctag tcgtcgcgca    180
ccgcagacgg gtattgtgga tgaatgctgt ttccgcagct gcgatctgcg tcgcctggaa    240
atgtactgtg cgccgctgaa accggcgaaa tctgcctaat aa                        282
```

<210> SEQ ID NO 13
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 13

Met Lys Arg Lys Lys Gly Lys Gly Leu Gly Lys Lys Arg Asp Pro
1               5                   10                  15

Ser Leu Arg Lys Tyr Lys Gly Pro Glu Thr Leu Cys Gly Ala Glu Leu
                20                  25                  30
```

```
Val Asp Ala Leu Gln Phe Val Cys Gly Asp Arg Gly Phe Tyr Phe Asn
         35                  40                  45

Lys Pro Thr Gly Tyr Gly Ser Ser Arg Arg Ala Pro Gln Thr Gly
 50                  55                  60

Ile Val Asp Glu Cys Cys Phe Arg Ser Cys Asp Leu Arg Arg Leu Glu
 65                  70                  75                  80

Met Tyr Cys Ala Pro Leu Lys Pro Ala Lys Ser Ala
                 85                  90
```

<210> SEQ ID NO 14
<211> LENGTH: 282
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atgaagcgta agaaaaaagg caaaggtctg ggcaaaaaac gtgatccgag cctgcgcaaa      60
tataaaggtc cggaaaccct gtgcggcgca gaactggtgg atgcgctgca gtttgtttgt     120
ggtgatcgtg gctttttattt caacaaaccg accggttacg gtagctctag tcgtcgcgca    180
ccgcagacgg gtattgtgga tgaatgctgt ttccgcagct gcgatctgcg tcgcctggaa     240
aactactgtg cgccgctgaa accggcgaaa tctgcctaat aa                        282
```

<210> SEQ ID NO 15
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Met Lys Arg Lys Lys Lys Gly Lys Gly Leu Gly Lys Lys Arg Asp Pro
  1               5                  10                  15

Ser Leu Arg Lys Tyr Lys Gly Pro Glu Thr Leu Cys Gly Ala Glu Leu
                 20                  25                  30

Val Asp Ala Leu Gln Phe Val Cys Gly Asp Arg Gly Phe Tyr Phe Asn
         35                  40                  45

Lys Pro Thr Gly Tyr Gly Ser Ser Arg Arg Ala Pro Gln Thr Gly
 50                  55                  60

Ile Val Asp Glu Cys Cys Phe Arg Ser Cys Asp Leu Arg Arg Leu Glu
 65                  70                  75                  80

Asn Tyr Cys Ala Pro Leu Lys Pro Ala Lys Ser Ala
                 85                  90
```

<210> SEQ ID NO 16
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Met Lys Arg Lys Lys Lys Gly Lys Gly Leu Gly Lys Lys Arg Asp Pro
  1               5                  10                  15

Ser Leu Arg Lys Tyr Lys Gly Pro Glu Thr Leu Cys Gly Ala Glu Leu
                 20                  25                  30
```

```
Val Asp Ala Leu Gln Phe Val Cys Gly Pro Arg Gly Phe Tyr Phe Asn
         35                  40                  45

Lys Pro Thr Gly Tyr Gly Ser Ser Ile Arg Arg Ala Pro Gln Thr Gly
 50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Thr Lys Ser Ala
                 85                  90
```

<210> SEQ ID NO 17
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Lys Arg Lys Lys Gly Lys Gly Leu Gly Lys Lys Arg Asp Pro Ser
 1               5                  10                  15

Leu Arg Lys Tyr Lys Gly Pro Glu Thr Leu Cys Gly Ala Glu Leu Val
                 20                  25                  30

Asp Ala Leu Gln Phe Val Cys Gly Pro Arg Gly Phe Tyr Phe Asn Lys
                 35                  40                  45

Pro Thr Gly Tyr Gly Ser Ser Ile Arg Arg Ala Pro Gln Thr Gly Ile
 50                  55                  60

Val Asp Glu Cys Cys Phe Arg Ser Cys Asp Leu Arg Arg Leu Glu Met
65                  70                  75                  80

Tyr Cys Ala Pro Leu Lys Pro Thr Lys Ser Ala
                 85                  90
```

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Lys Arg Lys Lys Lys Gly Lys Gly Leu Gly Lys Lys Arg Asp Pro
 1               5                  10                  15

Ser Leu Arg Lys Tyr Lys Gly Pro Glu Thr Leu Cys Gly Ala Glu Leu
                 20                  25                  30

Val Asp Ala Leu Gln Phe Val Cys Gly Asp Arg Gly Phe Tyr Phe Asn
                 35                  40                  45

Lys Pro Thr Gly Tyr Gly Ser Ser Arg Arg Ala Pro Gln Thr Gly
 50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Ala Lys Ser Ala Arg Ser Val Arg
                 85                  90                  95

Ala Gln Arg His Thr Asp Met Pro Lys Thr Gln Lys Glu Val His Leu
                100                 105                 110

Lys Asn Ala Ser Arg Gly Ser Ala
                115                 120
```

<210> SEQ ID NO 19
<211> LENGTH: 119

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Lys Arg Lys Lys Lys Gly Lys Gly Leu Gly Lys Lys Arg Asp Pro Ser
1               5                   10                  15

Leu Arg Lys Tyr Lys Gly Pro Glu Thr Leu Cys Gly Ala Glu Leu Val
            20                  25                  30

Asp Ala Leu Gln Phe Val Cys Gly Asp Arg Gly Phe Tyr Phe Asn Lys
        35                  40                  45

Pro Thr Gly Tyr Gly Ser Ser Ser Arg Arg Ala Pro Gln Thr Gly Ile
    50                  55                  60

Val Asp Glu Cys Cys Phe Arg Ser Cys Asp Leu Arg Arg Leu Glu Met
65                  70                  75                  80

Tyr Cys Ala Pro Leu Lys Pro Ala Lys Ser Ala Arg Ser Val Arg Ala
                85                  90                  95

Gln Arg His Thr Asp Met Pro Lys Thr Gln Lys Glu Val His Leu Lys
            100                 105                 110

Asn Ala Ser Arg Gly Ser Ala
            115

<210> SEQ ID NO 20
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Lys Arg Lys Lys Lys Gly Lys Gly Leu Gly Lys Lys Arg Asp Pro
1               5                   10                  15

Ser Leu Arg Lys Tyr Lys Gly Pro Glu Thr Leu Cys Gly Ala Glu Leu
            20                  25                  30

Val Asp Ala Leu Gln Phe Val Cys Gly Asp Arg Gly Phe Tyr Phe Asn
        35                  40                  45

Lys Pro Thr Gly Tyr Gly Ser Ser Ser Arg Arg Ala Pro Gln Thr Gly
    50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Ala Lys Ser Ala
                85                  90

<210> SEQ ID NO 21
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Lys Arg Lys Lys Lys Gly Lys Gly Leu Gly Lys Lys Arg Asp Pro Ser
1               5                   10                  15

Leu Arg Lys Tyr Lys Gly Pro Glu Thr Leu Cys Gly Ala Glu Leu Val
            20                  25                  30

Asp Ala Leu Gln Phe Val Cys Gly Asp Arg Gly Phe Tyr Phe Asn Lys

```
                35                  40                  45
Pro Thr Gly Tyr Gly Ser Ser Arg Arg Ala Pro Gln Thr Gly Ile
 50                  55                  60

Val Asp Glu Cys Cys Phe Arg Ser Cys Asp Leu Arg Arg Leu Glu Met
 65                  70                  75                  80

Tyr Cys Ala Pro Leu Lys Pro Ala Lys Ser Ala
                 85                  90

<210> SEQ ID NO 22
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Lys Arg Lys Lys Gly Lys Gly Leu Gly Lys Lys Arg Asp Pro
 1               5                  10                  15

Ser Leu Arg Lys Tyr Lys Met Glu Gly Pro Glu Thr Leu Cys Gly Ala
                 20                  25                  30

Glu Leu Val Asp Ala Leu Gln Phe Val Cys Gly Asp Arg Gly Phe Tyr
             35                  40                  45

Phe Asn Lys Pro Thr Gly Tyr Gly Ser Ser Ser Arg Arg Ala Pro Gln
 50                  55                  60

Thr Gly Ile Val Asp Glu Cys Cys Phe Arg Ser Cys Asp Leu Arg Arg
 65                  70                  75                  80

Leu Glu Met Tyr Cys Ala Pro Leu Lys Pro Ala Lys Ser Ala
                 85                  90

<210> SEQ ID NO 23
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Lys Arg Lys Lys Gly Lys Gly Leu Gly Lys Lys Arg Asp Pro Ser
 1               5                  10                  15

Leu Arg Lys Tyr Lys Met Glu Gly Pro Glu Thr Leu Cys Gly Ala Glu
                 20                  25                  30

Leu Val Asp Ala Leu Gln Phe Val Cys Gly Asp Arg Gly Phe Tyr Phe
             35                  40                  45

Asn Lys Pro Thr Gly Tyr Gly Ser Ser Ser Arg Arg Ala Pro Gln Thr
 50                  55                  60

Gly Ile Val Asp Glu Cys Cys Phe Arg Ser Cys Asp Leu Arg Arg Leu
 65                  70                  75                  80

Glu Met Tyr Cys Ala Pro Leu Lys Pro Ala Lys Ser Ala
                 85                  90

<210> SEQ ID NO 24
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24
```

Met Lys Arg Lys Lys Gly Lys Gly Leu Gly Lys Arg Asp Pro
1               5                   10                  15

Ser Leu Arg Lys Tyr Lys Thr Leu Cys Gly Ala Glu Leu Val Asp Ala
                20                  25                  30

Leu Gln Phe Val Cys Gly Asp Arg Gly Phe Tyr Phe Asn Lys Pro Thr
            35                  40                  45

Gly Tyr Gly Ser Ser Ser Arg Arg Ala Pro Gln Thr Gly Ile Val Asp
        50                  55                  60

Glu Cys Cys Phe Arg Ser Cys Asp Leu Arg Arg Leu Glu Met Tyr Cys
65                  70                  75                  80

Ala Pro Leu Lys Pro Ala Lys Ser Ala
                85

<210> SEQ ID NO 25
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Lys Arg Lys Lys Gly Lys Gly Leu Gly Lys Arg Asp Pro Ser
1               5                   10                  15

Leu Arg Lys Tyr Lys Thr Leu Cys Gly Ala Glu Leu Val Asp Ala Leu
                20                  25                  30

Gln Phe Val Cys Gly Asp Arg Gly Phe Tyr Phe Asn Lys Pro Thr Gly
            35                  40                  45

Tyr Gly Ser Ser Ser Arg Arg Ala Pro Gln Thr Gly Ile Val Asp Glu
        50                  55                  60

Cys Cys Phe Arg Ser Cys Asp Leu Arg Arg Leu Glu Met Tyr Cys Ala
65                  70                  75                  80

Pro Leu Lys Pro Ala Lys Ser
                85

<210> SEQ ID NO 26
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gly Pro Glu Thr Leu Cys Gly Ala Glu Leu Val Asp Ala Leu Gln Phe
1               5                   10                  15

Val Cys Gly Pro Arg Gly Phe Tyr Phe Asn Lys Pro Thr Gly Tyr Gly
                20                  25                  30

Ser Ser Ile Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Thr Lys Ser Ala Met Lys Arg Lys Lys Gly Lys Gly Leu
65                  70                  75                  80

Gly Lys Lys Arg Asp Pro Ser Leu Arg Lys Tyr Lys
                85                  90

<210> SEQ ID NO 27

```
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gly Pro Glu Thr Leu Cys Gly Ala Glu Leu Val Asp Ala Leu Gln Phe
1               5                  10                  15

Val Cys Gly Pro Arg Gly Phe Tyr Phe Asn Lys Pro Thr Gly Tyr Gly
            20                  25                  30

Ser Ser Ile Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Thr Lys Ser Ala Lys Arg Lys Lys Gly Lys Gly Leu Gly
65                  70                  75                  80

Lys Lys Arg Asp Pro Ser Leu Arg Lys Tyr Lys
                85                  90

<210> SEQ ID NO 28
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Pro Glu Thr Leu Cys Gly Ala Glu Leu Val Asp Ala Leu Gln Phe
1               5                  10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Met Lys Arg Lys Lys Lys Gly Lys Gly Leu Gly Lys Lys Arg
            100                 105                 110

Asp Pro Ser Leu Arg Lys Tyr Lys
            115                 120

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gly Pro Glu Thr Leu Cys Gly Ala Glu Leu Val Asp Ala Leu Gln Phe
1               5                  10                  15

Val Cys Gly Asp Arg Gly Phe Tyr Phe Asn Lys Pro Thr Gly Tyr Gly
            20                  25                  30
```

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
 50                  55                  60

Lys Pro Ala Lys Ser Ala Arg Ser Val Arg Ala Gln Arg His Thr Asp
 65                  70                  75                  80

Met Pro Lys Thr Gln Lys Glu Val His Leu Lys Asn Ala Ser Arg Gly
                 85                  90                  95

Ser Ala Lys Arg Lys Lys Gly Lys Gly Leu Gly Lys Lys Arg Asp
             100                 105                 110

Pro Ser Leu Arg Lys Tyr Lys
        115

<210> SEQ ID NO 30
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
             20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
 50                  55                  60

Lys Pro Ala Lys Ser Ala Met Lys Arg Lys Lys Gly Lys Gly Leu
 65                  70                  75                  80

Gly Lys Lys Arg Asp Pro Ser Leu Arg Lys Tyr Lys
             85                  90

<210> SEQ ID NO 31
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
             20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala Lys Arg Lys Lys Gly Lys Gly Leu Gly
 65                  70                  75                  80

Lys Lys Arg Asp Pro Ser Leu Arg Lys Tyr Lys
             85                  90

<210> SEQ ID NO 32
<211> LENGTH: 94

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Glu Gly Pro Glu Thr Leu Cys Gly Ala Glu Leu Val Asp Ala Leu
1               5                   10                  15

Gln Phe Val Cys Gly Asp Arg Gly Phe Tyr Phe Asn Lys Pro Thr Gly
            20                  25                  30

Tyr Gly Ser Ser Ser Arg Arg Ala Pro Gln Thr Gly Ile Val Asp Glu
        35                  40                  45

Cys Cys Phe Arg Ser Cys Asp Leu Arg Arg Leu Glu Met Tyr Cys Ala
    50                  55                  60

Pro Leu Lys Pro Ala Lys Ser Ala Met Lys Arg Lys Lys Lys Gly Lys
65                  70                  75                  80

Gly Leu Gly Lys Lys Arg Asp Pro Ser Leu Arg Lys Tyr Lys
                85                  90

<210> SEQ ID NO 33
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Glu Gly Pro Glu Thr Leu Cys Gly Ala Glu Leu Val Asp Ala Leu
1               5                   10                  15

Gln Phe Val Cys Gly Asp Arg Gly Phe Tyr Phe Asn Lys Pro Thr Gly
            20                  25                  30

Tyr Gly Ser Ser Ser Arg Arg Ala Pro Gln Thr Gly Ile Val Asp Glu
        35                  40                  45

Cys Cys Phe Arg Ser Cys Asp Leu Arg Arg Leu Glu Met Tyr Cys Ala
    50                  55                  60

Pro Leu Lys Pro Ala Lys Ser Ala Lys Arg Lys Lys Lys Gly Lys Gly
65                  70                  75                  80

Leu Gly Lys Lys Arg Asp Pro Ser Leu Arg Lys Tyr Lys
                85                  90

<210> SEQ ID NO 34
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Ala Met Lys Arg Lys Lys Lys Gly Lys Gly Leu Gly Lys Lys
```

-continued

```
                65                  70                  75                  80
Arg Asp Pro Ser Leu Arg Lys Tyr Lys
                            85

<210> SEQ ID NO 35
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Thr Leu Cys Gly Ala Glu Leu Val Asp Ala Leu Gln Phe Val Cys Gly
1               5                   10                  15

Asp Arg Gly Phe Tyr Phe Asn Lys Pro Thr Gly Tyr Gly Ser Ser Ser
            20                  25                  30

Arg Arg Ala Pro Gln Thr Gly Ile Val Asp Glu Cys Cys Phe Arg Ser
        35                  40                  45

Cys Asp Leu Arg Arg Leu Glu Met Tyr Cys Ala Pro Leu Lys Pro Ala
    50                  55                  60

Lys Ser Lys Arg Lys Lys Lys Gly Lys Gly Leu Gly Lys Lys Arg Asp
65                  70                  75                  80

Pro Ser Leu Arg Lys Tyr Lys
                        85
```

SELECTIVE CARTILAGE THERAPY

CROSS REFERENCE TO RELATED APPLICATIONS

This application is a 35 U.S.C. §371 National Phase Entry Application of International Application No. PCT/US2013/047556 filed Jun. 25, 2013, which designates the U.S., and which claims benefit under 35 U.S.C. §119(e) of U.S. Provisional Application No. 61/663,686 filed on Jun. 25, 2012, and U.S. Provisional Application No. 61/750,999 filed on Jan. 10, 2013, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 18, 2014, is named 043214-076573-US_SL.txt and is 30,277 bytes in size.

BACKGROUND OF THE INVENTION

Systemic administration or non-specific activity of therapeutic agents, such as recombinant cytokines and small molecules, for the treatment of cartilage-associated disorders or injuries can trigger off-target selequae. Thus there remains a need for targeted delivery of the active molecules to the site of interest.

SUMMARY OF THE INVENTION

The present embodiments provide for the selective delivery of recombinant therapeutic proteins or small molecules to cartilage cells or cartilage tissues or that express proteoglycans, for example, but not limited to cartilage, brain and spinal cord tissue, skin and subcutaneous tissue. More specifically, embodiments herein are directed to a heparin-binding peptide (HB) conjugated (e.g., fused) to Insulin-like growth factor 1 (IGF-1) or a functional portion, variant, derivative, or analog thereof to form an HB-IGF-1 fusion protein. In a particular embodiment, the HB peptide has the amino acids MKRKKKGKGLGKKRDPSLRKYK (SEQ ID NO:1) or KRKKKGKGLGKKRDPSLRKYK (SEQ ID NO:2). In some embodiments, a HB portion of the HB-IGF-1 fusion protein composition is positively charged through many lysine and arginine residues in the HB peptide, which binds to cellular or tissue expressing proteoglycans which are negatively charged by sulfate groups.

Another aspect of the present invention provides for a method of treating cartilage-related clinical conditions (e.g., damage or disease) comprising administering to a subject an effective amount of a recombinant fusion protein comprising HB-X, where X is a therapeutic protein or a functional portion, derivative, analog or variant thereof. In particular embodiments, the therapeutic protein is IGF-1.

In some embodiments, the cartilage condition is a articular cartilage defect including rupture or detachment, a meniscal defect including a partial or complete tear, Osteoarthritis, Traumatic cartilage rupture or detachment, Ankylosing spondylitis, Capsulitis, Psoriatic arthritis, Rheumatoid arthritis, Systemic lupus erythematosus, or X-linked hypophosphatemic rickets, or Juvenile idiopathic arthritis. Treatment of cartilage condition can be combined with other therapy as an adjunct to other surgical interventions for articular cartilage repair, meniscal repair, or ligament repair, for the purposes of both improving the repair and preventing development of osteoarthritis.

DETAILED DESCRIPTION OF THE INVENTION

Figure 1:
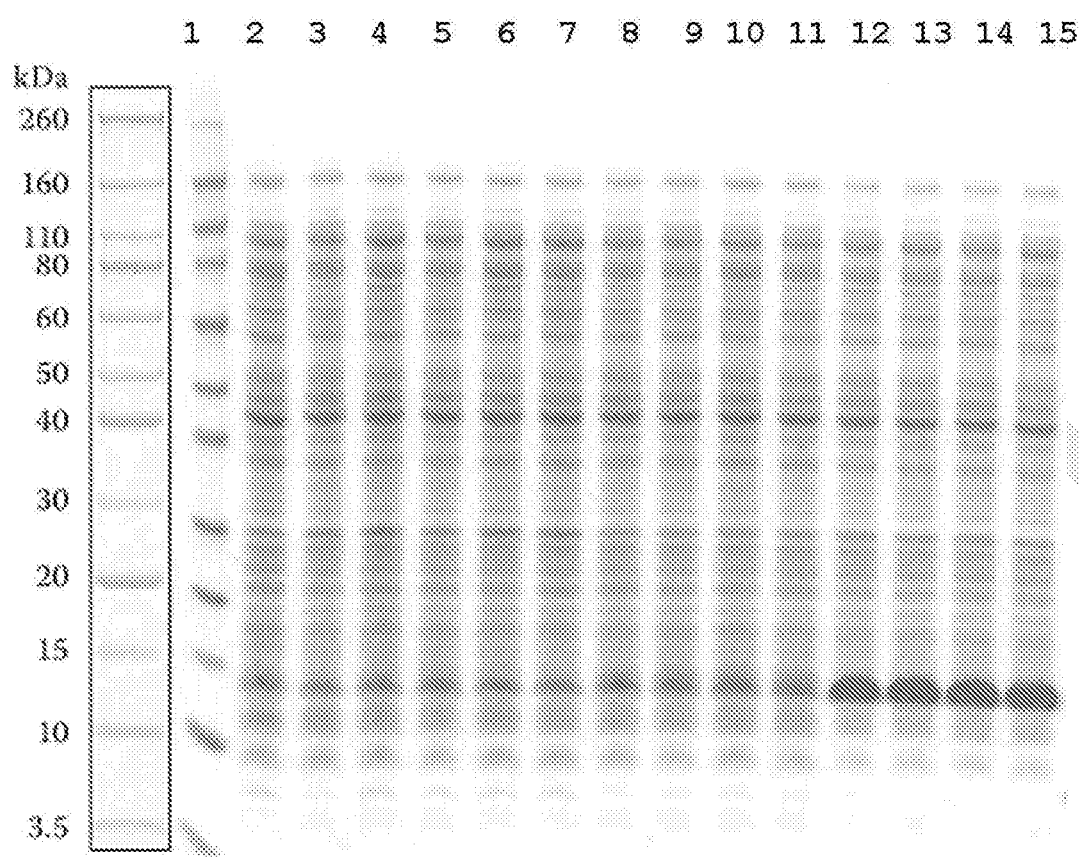
FIG. 1 shows a SDS-PAGE gel showing relative expression levels of various HB-IGF-1 constructs in *E. coli*. Lane 1, Novex Sharp Standard; lane 2, Uninduced pET24a; lane 3, Induced blank pET24a; lanes 4-7, Rat "Wildtype" (WT); lanes 8-11, WT HB-IGF-1; lanes 12-15, mutant HB-IGF-1 C17S.

The present invention related to conjugation of a heparin-binding (HB) peptides comprising SEQ ID NO: 1 or 2 to Insulin-like growth factor 1 (IGF-1) or a functional portion, variant, derivative, or analog thereof to form an HB-IGF-1 fusion protein for selectively delivery of IGF-1 to a cell or tissue expressing proteoglycans. In some embodiments, the HB-IGF-1 fusion protein can be used to deliver the IGF-1 to cells or tissues that express proteoglycans, for example, but not limited to cartilage, brain and spinal cord tissue, skin and subcutaneous tissue.

More specifically, some embodiments herein are directed to heparin-binding peptides (HB) of SEQ ID NO: 1 or 2 fused to IGF-1 or a functional portion, variant, derivative, or analog thereof, optionally by a linker peptide.

An aspect of the present invention provides for a therapeutic composition comprising a recombinant fusion protein comprising HB-IGF-1$_n$, or (HB)$_n$-IGF-1$_n$, where HB is a heparin binding protein of SEQ ID NO: 1 or 2, and IGF-1 is an insulin-like growth factor 1 protein or a functional portion, variant, derivative, or analog thereof, and n is an integer of at least 1. Any combination of a HB peptide selected from the group of SEQ ID NO: 1 or 2 can be used in a composition of a HB-IGF-1 fusion protein, where the HB peptide can be located at the N- and/or C-terminus of the IGF-1 protein, and there can be one or multiple HB peptide-linkers attached to the N- and/or C-terminus of the IGF-1 protein.

In some embodiments, the composition can comprise a mixture of HB-IGF-1 constructs, wherein IGF-1 represents different forms of IGF-1 proteins (e.g., IGF-1, or functional fragments, variants, derivatives, or analogs thereof) i.e., a composition comprising HB-IGF1$^1$ and HB-IGF$^2$, etc.).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims. Unless defined otherwise, all technical and scientific terms used herein have the same meaning as those commonly understood to one of ordinary skill in the art to which this invention pertains. All Gene IDs refer to human genes, unless otherwise noted, available in the National Center for Biotechnology Information (NCBI) database.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about." It is further to be understood that all base sizes or amino acid sizes, and all molecular weight or molecular mass values, given for nucleic acids or polypeptides are approximate, and are provided for description.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention provides for selective delivery of IGF-1 therapeutic proteins to particular tissues to which heparin binding proteins associate. More specifically, the present embodiments provide for a proteinaceous heparin-binding motif (HB) that is fused to a therapeutic protein such as IGF-1 or functional portion, analog, variant, or derivative thereof.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

The term "protein" may be used interchangeably with "polypeptide" to refer to a polymer of amino acid residues linked by peptide bonds. Typically, a protein or polypeptide has a minimum length of at least 25 amino acids. The term "polypeptide" and "protein" can encompass a multimeric protein, e.g., a protein containing more than one domain or subunit. The term "peptide" as used herein typically refers to a peptide bond-linked amino acid polymer containing less than 25 amino acids, e.g., between about 4 amino acids and about 25 amino acids in length. Proteins and peptides can be composed of linearly arranged amino acids linked by peptide bonds, whether produced biologically, recombinantly, or synthetically and whether composed of naturally occurring or non-naturally occurring amino acids, are included within this definition. Both full-length proteins and fragments thereof greater than 25 amino acids are encompassed by the definition of protein. The terms also include polypeptides that have co-translational (e.g., signal peptide cleavage) and post-translational modifications of the polypeptide, such as, for example, disulfide-bond formation, glycosylation, acetylation, phosphorylation, lipidation, proteolytic cleavage (e.g., cleavage by metalloproteases), and the like. Furthermore, as used herein, a "polypeptide" refers to a protein that includes modifications, such as deletions, additions, and substitutions (generally conservative in nature as would be known to a person in the art) to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, has a well-defined conformation. Proteins, as opposed to peptides, generally consist of chains of 25 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 25 amino acids in length.

It will be appreciated that proteins, polypeptides, or peptides often contain amino acids other than the 20 amino acids commonly referred to as the 20 naturally occurring amino acids (e.g., synthetic non-native amino acids), and that many amino acids, including the terminal amino acids, can be modified in a given polypeptide, either by natural processes such as glycosylation and other post-translational modifications, or by chemical modification techniques which are well known in the art. Known modifications which can be present in polypeptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "variant" refers to a polypeptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule Amino acid substitutions include alterations in which an amino acid is replaced with a different naturally-occurring or a non-conventional amino acid residue. Such substitutions may be classified as "conservative," in which case an amino acid residue contained in a polypeptide is replaced with another naturally occurring amino acid of similar character either in relation to polarity, side chain functionality or size. Substitutions encompassed by variants as described herein may also be "non-conservative," in which an amino acid residue which is present in a peptide is substituted with an amino acid having different properties (e.g., substituting a charged or hydrophobic amino acid with alanine), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide).

Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. "Conservative amino acid substitutions" result from replacing one amino acid with another that has similar structural and/or chemical properties. Conservative substitution tables providing functionally similar amino acids are well known in the art. For example, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). See, e.g., Creighton, PROTEINS (W.H. Freeman & Co., 1984). The choice of conservative amino acids may be selected based on the location of the amino acid to be substituted in the peptide, for example if the amino acid is on the exterior of the peptide and exposed to solvents, or on the interior and not exposed to solvents. In some embodiments, polypeptides including non-conservative amino acid substitutions are also encompassed within the term "variants." As used herein, the term "non-conservative" substitution refers to substituting an amino acid residue for a different amino acid residue that has different chemical properties. Non-limiting examples of non-conservative substitutions include aspartic acid (D) being replaced with glycine (G); asparagine (N) being replaced with lysine (K); and alanine (A) being replaced with arginine (R). Selection of such conservative and non-conservative amino acid substitutions is within the skill of one of ordinary skill in the art.

The term "derivative" as used herein refers to proteins or peptides which have been chemically modified, for example by ubiquitination, labeling, pegylation (derivatization with polyethylene glycol) or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, or eliminate or attenuate an undesirable side effect of the molecule, etc. Moieties capable of mediating such effects are disclosed in REMINGTON'S PHARMACEUTICAL SCIENCES (21st ed., Tory, ed., Lippincott Williams & Wilkins, Baltimore, Md., 2006).

The term "functional" when used in conjunction with "derivative" or "variant" or "fragment" refers to a protein molecule which possesses a biological activity that is substantially similar to a biological activity of the entity or molecule of which it is a derivative or variant. "Substantially similar" in this context means that the biological activity of a polypeptide, is at least 50% as active as a reference, e.g., a corresponding wild-type polypeptide, e.g., at least 60% as active, 70% as active, 80% as active, 90% as active, 95% as active, 100% as active or even higher (i.e., the variant or derivative has greater activity than the wild-type), e.g., 110% as active, 120% as active, or more, inclusive.

The term "functional portion" or "functional fragment" refers to a portion of the native molecule (e.g., the native protein or receptor binding moiety of a chemical entity) that mediates the same effect as the full-length molecule, e.g., stimulates a cell response such as growth or affects a signal or signal cascade related to a desired physiological effect.

The term "fragment" of a peptide, polypeptide or molecule as used herein refers to any contiguous polypeptide subset of the molecule. The term "protein fragment" as used herein includes both synthetic and naturally-occurring amino acid sequences derivable from the naturally occurring amino acid sequence, e.g., a naturally occurring IGF-1 protein (SEQ ID NO: 3 or 4) or a variant thereof (e.g., SEQ ID NO: 5-7). The protein is said to be "derivable from the naturally-occurring amino acid sequence" if it can be obtained by fragmenting the naturally-occurring protein, or if it can be synthesized based upon a knowledge of the sequence of the naturally occurring amino acid sequence or of the genetic material (DNA or RNA) which encodes this sequence. Accordingly, a "fragment" of a molecule, is meant to refer to any polypeptide subset of the molecule. Fragments of IGF-1 peptide which have the activity of IGF-1 peptide variants of SEQ ID NO: 4-7 as disclosed herein and which are soluble are also encompassed for use in the present invention.

For example functional fragments of SEQ ID NO: 3-7 useful in the methods as disclosed herein have at least 30% the activity as that of a polypeptide of SEQ ID NO: 3-7 in vivo. Stated another way, a fragment of SEQ ID NO: 4 or SEQ ID NO: 5 or SEQ ID NO:6 or SEQ ID NO: 7 is any fragment which, alone or fused to a HB-peptide as disclosed herein can result in at least 30% of the same activity as compared to SEQ ID NO: 4 or SEQ ID NO: 5 or SEQ ID NO:6 or SEQ ID NO: 7 to treat an cartilage-related disease or condition (as disclosed in the Examples). A "fragment" can be at least about 6, at least about 9, at least about 15, at least about 20, at least about 30, least about 40, at least about 50, at least about 100, at least about 250, at least about 300 nucleic or amino acids, and all integers in between. Exemplary fragments include C-terminal truncations, N-terminal truncations, or truncations of both C- and N-terminals (e.g., deletions of, for example, at least 1, at least 2, at least 3, at least 4, at least 5, at least 8, at least 10, at least 15, at least 20, at least 25, at least 40, at least 50, at least 75, at least 100 or more amino acids deleted from the N-termini, the C-termini, or both). One of ordinary skill in the art can create such fragments by simple deletion analysis. Such a fragment of SEQ ID NO: 4 or SEQ ID NO: 5 or SEQ ID NO:6 or SEQ ID NO: 7 can be, for example, 1, 2, 3, 4, 5, 6, 7, 8, 9 or 10 amino acids or more than 10 amino acids, deleted from the N-terminal and/or C-terminal of SEQ ID NO: 4 or SEQ ID NO: 5 or SEQ ID NO:6 or SEQ ID NO: 7, respectively. In some embodiments, by sequentially deleting N- and/or C-terminal amino acids from SEQ ID NO: 4 or SEQ ID NO: 5 or SEQ ID NO:6 or SEQ ID NO: 7, and assessing the function of the resulting peptide fragment, alone or fused to an active agent can identify a functional fragment of HB for use in the present invention. One can create functional fragments with multiple smaller fragments. These can be attached by bridging peptide linkers. One can readily select linkers to maintain wild type conformation. One of ordinary skill in the art can easily assess the function of an HB-IGF-1 fusion protein to retain in the tissue and cause a biological effect by the IGF-1 protein (as disclosed in the Examples) as compared to a HB-IGF-1 fusion protein comprising SEQ ID NO: 4 or SEQ ID NO: 5 or SEQ ID NO:6 or SEQ ID NO: 7. Using an in vivo assay such as the cartilage assay as disclosed in the Examples, if the HB-IGF-1 fusion protein comprising an IGF-1 peptide fragment has at least 30% of the biological activity of the HB-IGF-1 corresponding to SEQ ID NO: 13 or SEQ ID NO: 15 as disclosed herein, then the IGF-1 fragment is considered a valid functional fragment of IGF-1 and can used in HB-IGF-1 fusion proteins and methods as disclosed herein. In some embodiments, a fragment of SEQ ID NO: 4 or SEQ ID NO: 5 or SEQ ID NO:6 or SEQ ID NO: 7 can be less than 20, or less than 15 or less than 10, or less than 5 amino acids of SEQ ID NO: 4 or SEQ ID NO: 5 or SEQ ID NO:6 or SEQ ID NO: 7. However, as stated above, the fragment must be at least 4 amino acids, at least about 9, at least about 15, at least about 20, at least about 30, at least about 40, at least about 50, at least about 100, at least about 250, at least about 500 nucleic acids or amino acids, or any integers in between.

The term "wild type" refers to the naturally-occurring, normal polynucleotide sequence encoding a protein, or a portion thereof, or protein sequence, or portion thereof, respectively, as it normally exists in vivo. The term "mutant" refers to an organism or cell with any change in its genetic material, in particular a change (i.e., deletion, substitution, addition, or alteration) relative to a wild-type polynucleotide sequence or any change relative to a wild-type protein sequence. The term "variant" may be used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

The term "substantially similar," when used in reference to a variant of a protein or peptide or a functional derivative thereof, as compared with the original protein, means that a particular subject sequence varies from the sequence of the polypeptide by one or more substitutions, deletions, or additions, but retains at least 50%, or higher, e.g., at least 60%, 70%, 80%, 90% or more, inclusive, of the function of the protein. In determining polynucleotide sequences, all subject polynucleotide sequences capable of encoding substantially similar amino acid sequences are considered to be substantially similar to a reference polynucleotide sequence, regardless of differences in codon sequence. A nucleotide sequence is "substantially similar" to a given nucleic acid sequence if: (a) the given polynucleotide nucleotide hybridizes to the coding regions of the native polynucleotide, or (b) the given polynucleotide is capable of hybridization to the native polynucleotide under moderately stringent conditions and its encoded protein has biological activity similar to the native protein; or (c) the sequence of polynucleotide are degenerate as a result of the genetic code relative to the nucleotide sequences defined in (a) or (b). Substantially similar proteins will typically be greater than about 80% similar to the corresponding sequence of the native protein.

The terms "homologous" or "homologues" are used interchangeably, and when used to describe a polynucleotide or polypeptide, indicate that two polynucleotides or polypeptides, or designated sequences thereof, when optimally aligned and compared, for example using BLAST, version 2.2.14 with default parameters for an alignment are identical, with appropriate nucleotide insertions or deletions or amino-acid insertions or deletions, typically in at least 70% of the nucleotides of the nucleotides for high homology. For a polypeptide, there should be at least 30% of amino acid identity in the polypeptide, or at least 50% for higher homology. The term "homolog" or "homologous" as used herein also refers to homology with respect to structure. Determination of homologs of genes or polypeptides can be easily ascertained by the skilled artisan. When in the context with a defined percentage, the defined percentage homology means at least that percentage of amino acid similarity. For example, 85% homology refers to at least 85% of amino acid similarity.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Where necessary or desired, optimal alignment of sequences for comparison can be conducted by any variety of approaches, as these are well-known in the art.

The term "heterologous" in reference to nucleic acid sequences, proteins or polypeptides, means that these molecules are not naturally occurring in that cell. For example, the nucleic acid sequence coding for a fusion protein described herein that is inserted into a cell, e.g. in the context of a protein expression vector, is a heterologous nucleic acid sequence.

As used herein, the term "fused" means that at least one protein or peptide is physically associated with a second protein or peptide. In some embodiments, fusion is typically a covalent linkage, however, other types of linkages are encompassed in the term "fused" include, for example, linkage via an electrostatic interaction, or a hydrophobic interaction and the like. Covalent linkage can encompass linkage as a fusion protein or chemically coupled linkage, for example via a disulfide bound formed between two cysteine residues.

As used herein, the term "fusion polypeptide" or "fusion protein" means a protein created by joining two or more polypeptide sequences together. The fusion polypeptides encompassed in this invention include translation products of a chimeric gene construct that joins the DNA sequences encoding the HB peptide or mutants thereof, with the DNA sequence encoding a second polypeptide to form a single open-reading frame. In other words, a "fusion polypeptide" or "fusion protein" is a recombinant protein of two or more proteins which are joined by a peptide bond or via several peptides. The fusion protein may also comprise a peptide linker between the HB peptide and the IGF-1 therapeutic peptide or polypeptide of the fusion protein.

In some embodiments, fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. As a non-limiting example, the nucleic acid sequence encoding the HB peptide is fused in frame to an end, either the 5' or the 3' end, of a gene encoding a first fusion partner (e.g., such as a therapeutic IGF-1 protein or peptide). In this manner, on expression of the gene, the HB peptide is functionally expressed and fused to the N-terminal or C-terminal end of IGF-1. In certain embodiments, modification of the polypeptide probe is such that the functionality of the HB peptide remains substantially unaffected in terms of its biological activity by fusion to the IGF-1 protein or functional fragment thereof. In some embodiments, a nucleic acid construct encoding a HB-IGF-1 fusion protein also has a nucleic acid sequence which encodes a linker, which is located between nucleic acid encoding the HB peptide and the nucleic acid sequence encoding IGF-1. In some embodiments, the HB-IGF-1 fusion protein is configured such that the functionality of the HB peptide or IGF-1 protein or functional fragment thereof is not significantly compromised by the fusion.

As used herein, the term "associated with" means that one entity is in physical association or contact with another. Thus, a HB peptide "associated with" a IGF-1 can be either a covalent or non-covalent joining of the HB peptide to the IGF-1 protein or functional fragment thereof. The term "association" or "interaction" or "associated with" are used interchangeably herein and as used in reference to the association or interaction of a HB peptide with the IGF-1 protein or functional fragment thereof, either by a direct linkage or an indirect linkage.

As used herein, the term "conjugate" or "conjugation" or "linked" as used herein refers to the attachment of two or more entities to form one entity. For example, the methods of the present invention encompass the conjugation of a HB peptide joined with another entity, for example an IGF-1 protein or functional fragment thereof. As disclosed herein, the attachment can be by means covalent or non-covalent bonds, or protein fusion or by any means known to one skilled in the art. The joining can be permanent or reversible. Methods for conjugation are well known by persons skilled in the art and are encompassed for use in the present invention.

Alternatively, two or more entities that are joined can be linked by a direct linkage. A direct linkage includes any linkage wherein a linker moiety is not required. In one embodiment, a direct linkage includes a chemical or a physical interaction wherein the two moieties, i.e. the HB peptide and the IGF-1 protein or functional fragment thereof interact such that they are attracted to each other. Examples of direct interactions include covalent interactions, non-covalent interactions, hydrophobic/hydrophilic, ionic (e.g., electrostatic, coulombic attraction, ion-dipole, charge-transfer), Van der Waals, or hydrogen bonding, and chemical bonding, including the formation of a covalent bond. Accordingly, in one embodiment, a HB peptide and a IGF-1 protein or functional fragment thereof are not linked via a linker, e.g., they are directly linked. In a further embodiment, a HB peptide and IGF-1 protein or functional fragment thereof are electrostatically associated with each other.

The term "conjugated" refers to the attachment of at least two entities joined together. The joining of the two entities can be direct (e.g., via covalent or non-covalent bonds) or indirect (e.g., via linkers etc.)

The term "recombinant" when used to describe a nucleic acid molecule, means a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a peptide, polypeptide, protein, or recombinant fusion protein, means a polypeptide produced by expression from a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting or mediating expression of a heterologous nucleic acid to which it has been linked to a host cell; a plasmid is a species of the genus encompassed by the term "vector." The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA molecules which, in their vector form are not bound to the chromosome, and typically comprise entities for stable or transient expression or the encoded DNA. Other expression vectors that can be used in the methods as disclosed herein include, but are not limited to plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self-replicating extrachromosomal vectors or vectors which integrates into a host genome. Preferred vectors are those capable of autonomous replication and/or expression of nucleic acids to which they are linked.

The terms "subject" and "individual" are used interchangeably herein, and refer to an animal, for example a human, to whom treatment, including prophylactic treatment, with the pharmaceutical composition according to the present invention, is provided. The term "subject" as used herein refers to human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. The term does not denote a particular age or sex. Thus, adult and newborn subjects, as well as fetuses, whether male or female, are intended to be covered. Examples of subjects include humans, dogs, cats, cows, goats, and mice. The term subject is further intended to include transgenic species.

The term "tissue" is intended to include intact cells, blood, blood preparations such as plasma and serum, bones, joints, cartilage, neuronal tissue (brain, spinal cord and neurons), muscles, smooth muscles, and organs.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, inderdisposion, affection.

The term "cartilage-related condition" or "cartilage-related clinical condition" refers to any defect in the articular cartilage. The term encompasses, but is not limited to, a rupture or detachment of the cartilage, a meniscal defect including a partial or complete tear, damage or a disease effecting the meniscus and/or patella, osteoarthritis (referred to herein as "OA"), including knee, finger, wrist, hip, ankle, elbow, toe, shoulder, and spinal osteoarthritis, traumatic cartilage rupture or detachment, ankylosing spondylitis, capsulitis, psoriatic arthritis, rheumatoid arthritis (RA), systemic lupus erythematosus, juvenile idiopathic arthritis, Chondropathy, Chondrosarcoma, Chondromalacia, Polychondritis, Relapsing Polychondritis, Slipped epiphysis, Osteochondritis Dissecans, Chondrodysplasia, Costochondritis, X-linked hypophosphatemic rickets, Osteochondroma, Chondrosarcoma (malignant), Osteoarthritis Susceptibility (types 1-6), Spondylosis , Osteochondroses, Primary chondrosarcoma, Chondrodysplasia, Tietze syndrome, Dermochondrocorneal dystrophy of Francois, Epiphyseal dysplasia, multiple, (types 1-5), Ossified Ear cartilages with Mental deficiency, Muscle Wasting and Bony Changes, Carpotarsal osteochondromatosis, Achondroplasia, Chondrocalcinosis (types 1-2), Genochondromatosis, Chondrodysplasia (disorder of sex development), Chondroma, Achondrogenesis (types 1A, 1B, 2, 3, 4, Langer-Saldino Type), Type II Achondrogenesis-Hypochondrogenesis, Atelosteogenesis, (type 1, 2 and III), Pyknoachondrogenesis, Pseudoachondroplasia, Osteoarthropathy of fingers, familial, Diastrophic dysplasia, Dyschondrosteosis-nephritis, Coloboma of Alar-nasal cartilages with telecanthus, Alar cartilages hypoplasia—coloboma-telecanthus, Pierre Robin syndrome—fetal chondrodysplasia, Dysspondyloenchondromatosis, Achondroplasia regional—dysplasia abdominal muscle, Osteochondritis Dissecans, Familial Articular Chondrocalcinosis, Tracheobronchomalacia, Chondritis, Dyschondrosteosis, Maffucci Syndrome, Jequier-Kozlowski-skeletal dysplasia, Chondrodystrophy, Cranio osteoarthropathy, Tietze's syndrome, Hip dysplasia—enchondromata-enchondromata, Bessel-Hagen disease, Chondromatosis (benign), Enchondromatosis (benign), chondrocalcinosis due to apatite crystal deposition, Meyenburg-Altherr-Uehlinger syndrome, Enchondromatosis-dwarfism-deafness, Astley-Kendall syndrome, Synovial osteochondromatosis, Chondrocalcinosis familial articular, Severe achondroplasia with developmental delay and acanthosis nigricans, Chondrocalcinosis, Keutel syndrome, Stanescu syndrome, Fibrochondrogenesis, Hypochondroplasia, A "composition" or "pharmaceutical composition" are used interchangeably herein refers to a composition that usually contains an excipient, such as a pharmaceutically acceptable carrier that is conventional in the art and that is suitable for administration to a HB-IGF-1 conjugate to a tissue or subject. In addition, compositions for topical (e.g., oral mucosa, respiratory mucosa) and/or oral administration can form solutions, suspensions, tablets, pills, capsules, sustained-release formulations, oral rinses, or powders, as known in the art and described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21st Ed.

As used herein, the terms "treat," "treating," and "treatment" refer to the alleviation or measurable lessening of one or more symptoms or measurable markers of a cartilage-related condition, disease or disorder; while not intending to be limited to such, disease or disorders of particular interest include a cartilage-related disease or disorder as disclosed herein. Measurable lessening includes any statistically significant decline in a measurable marker or symptom. In some embodiments, treatment is prophylactic treatment.

The term "therapeutically effective amount" refers to an amount effective, at dosages and for periods of time necessary, to achieve the desired therapeutic result, e.g., a diminishment or prevention of effects associated with various disease states or conditions, such as reduce a symptom of an autoimmune disease in the subject. The term "therapeutically effective amount" refers to an amount of an HB-IGF-1 conjugate as disclosed herein effective to treat or prevent a disease or disorder in a mammal, preferably a human. A therapeutically effective amount of a HB-IGF-1 conjugate can vary according to factors such as the disease state, age, sex, and weight of the subject, and the ability of the therapeutic compound IGF-1 protein or functional fragment thereof to elicit a desired response in the subject. A therapeutically effective amount is also one in which any toxic or detrimental effects of the therapeutic agent are outweighed by the therapeutically beneficial effects. In some embodiments, a therapeutically effective amount is an 'effective amount", which as used herein refers to the amount of therapeutic agent of pharmaceutical composition to alleviate at least one or some of the symptoms of the disease or disorder. An "effective amount" for purposes herein is thus determined by such considerations as are known in the art and is the amount to achieve improvement including, but not limited to, improved survival rate or more rapid recovery, or improvement or elimination of at least one symptom and other indicator of the disease being treated which are appropriate measures by those skilled in the art. It should be noted that HB-IGF-1 fusion proteins as disclosed herein can be administered as a pharmaceutically acceptable salt and can be administered alone or as an active ingredient in combination with pharmaceutically acceptable carriers, diluents, adjuvants and vehicles.

The term "prophylactically effective amount" refers to an amount of a HB-IGF-1 conjugate which is effective, at dosages and for periods of time necessary, to achieve the desired prophylactic result. Typically, since a prophylactic dose of HB-IGF-1 conjugate is administered to a subject prior to, or at an earlier stage of a disease, and in some embodiments, a prophylactically effective amount is less than the therapeutically effective amount. A prophylatically effective amount of a HB-IGF-1 conjugate is also one in which any toxic or detrimental effects of the compound are outweighed by the beneficial effects.

As used herein, the terms "prevent," "preventing" and "prevention" refer to the avoidance or delay in manifestation of one or more symptoms or measurable markers of a disease or disorder, e.g., of an autoimmune disease. A delay in the manifestation of a symptom or marker is a delay relative to the time at which such symptom or marker manifests in a control or untreated subject with a similar likelihood or susceptibility of developing the disease or disorder. The terms "prevent," "preventing" and "prevention" include not only the avoidance or prevention of a symptom or marker of the disease, but also a reduced severity or degree of any one of the symptoms or markers of the disease, relative to those symptoms or markers in a control or non-treated individual with a similar likelihood or susceptibility of developing the disease or disorder, or relative to symptoms or markers likely to arise based on historical or statistical measures of populations affected by the disease or disorder. By "reduced severity" is meant at least a 10% reduction in the severity or degree of a symptom or measurable disease marker, relative to a control or reference, e.g., at least 15%, 20%, 30%, 40%, 50%, 60%, 70%, 80%, 90%, 95%, 99% or even 100% (i.e., no symptoms or measurable markers).

As used herein, the terms "administering," and "introducing" are used interchangeably herein and refer to the placement of HB-IGF-1 fusion protein or conjugate of the present invention into a subject by a method or route which results in at least partial localization of the HB-IGF-1 conjugate at a desired site. The compounds of the present invention can be administered by any appropriate route which results in an effective treatment in the subject.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of HB-IGF-1 such that it enters the animal's system and, thus, is subject to metabolism and other like processes, for example, subcutaneous administration.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

The term "reduced" or "reduce" or "decrease" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or least 60%, or least 70%, or least 80%, at least 90% or more, up to and including a 100% decrease (i.e., absent level as compared to a reference sample), or any decrease between 10-100% as compared to a reference level, as that term is defined herein.

The terms "increased" or "increase" as used herein generally mean an increase by a statically significant amount; such as a statistically significant increase of at least 10% as compared to a reference level, including an increase of at least 20%, at least 30%, at least 40%, at least 50%, at least 60%, at least 70%, at least 80%, at least 90%, at least 100% or more, inclusive, including, for example at least 2-fold, at least 3-fold, at least 4-fold, at least 5-fold, at least 10-fold increase or greater as compared to a reference level, as that term is defined herein.

The term "high" as used herein generally means a higher by a statically significant amount relative to a reference; such as a statistically significant value at least 10% higher than a reference level, for example at least 20% higher, at least 30% higher, at least 40% higher, at least 50% higher, at least 60% higher, at least 70% higher, at least 80% higher, at least 90% higher, at least 100% higher, inclusive, such as at least 2-fold higher, at least 3-fold higher, at least 4-fold higher, at least 5-fold higher, at least 10-fold higher or more, as compared to a reference level.

The term "subject" as used herein refers to any animal in which it is useful to modulate a response in a tissue targeted by the HB moiety of the composition. The subject can be a wild, domestic, commercial or companion animal such as a bird or mammal. The subject can be a human. Although in one embodiment of the invention it is contemplated that the therapeutic compositions as disclosed herein, can also be suitable for the therapeutic treatment in humans, it is also applicable to warm-blooded vertebrates, e.g., mammals, such as non-human primates, (particularly higher primates), sheep, dog, rodent (e.g., mouse or rat), guinea pig, goat, pig, cat, rabbits, cows, and non-mammals such as chickens, ducks, or turkeys. In some embodiments, the subject is an experimental animal or animal substitute as a disease model.

The term "pharmaceutically acceptable" refers to compounds and compositions which may be administered to mammals without undue toxicity. The term "pharmaceutically acceptable carriers" excludes tissue culture medium. Exemplary pharmaceutically acceptable salts include but are not limited to mineral acid salts such as hydrochlorides, hydrobromides, phosphates, sulfates, and the like, and the salts of organic acids such as acetates, propionates, malonates, benzoates, and the like. Pharmaceutically acceptable carriers are well-known in the art. Some pharmaceutically acceptable carriers may be used to provide for sustained release of the compositions described herein. For example, hyaluronic acid and hyaluronic acid gel forms are used in intra-articular injections, and can be used to provide for sustained release of the HB-X compositions.

As used herein, the terms "treating," "treatment", and "to treat" are used to indicate the production of beneficial or desired results, such as to alleviate symptoms, or eliminate the causation of a disease or disorder either on a temporary or a permanent basis, slow the appearance of symptoms and/or progression of the disorder, or prevent progression of disease. The terms "treat" or "treatment" refer to both therapeutic treatment and prophylactic or preventative measures. Beneficial or desired clinical results include, but are not limited to, alleviation of symptoms, diminishment of extent of autism, stabilized (i.e., not worsening) state of pathology involvement, delay or slowing of disease progression, amelioration or palliation of the disease state. An "effective regimen" is administered over an effective course (a sufficient treatment or amount over a sufficient period of time) to achieve level of desired results. Monitoring efficacy can be done by methods known in the art for the particular disease or its symptoms.

Heparin Binding Proteins (HB)

The present invention provides for a heparin-binding motif (HB) that is fused IGF-1 or a functional portion, variant, derivative, or analog thereof. In particular, the HB peptide comprises the amino acid residue sequence MKRK-KKGKGLGKKRDPSLRKYK (SEQ ID NO:1) or KRKK-KGKGLGKKRDPSLRKYK (SEQ ID NO:2). In some embodiments, the HB portion of the composition is positively charged through many lysine and arginine residues; and binds to cellular or tissue proteoglycans which are negatively charged by sulfate groups.

The compositions described herein are useful, for example, in cartilage repair. For example, traumatic injuries to the joint, such as those involving anterior cruciate ligament (ACL) rupture, lead to an increased risk for development of osteoarthritis. Furthermore, this risk may not be resolved by surgical restoration of function (Lohmander et al., 35 Am. J. Sports Med. 1756 (2007)), which may be related an the initial inflammatory and catabolic response following joint injury. Lohmander et al., 42 Arthritis Rheum. 534 (1999); Lohmander et al., 48 Arthritis Rheum. 3130 (2003); Irie et al., 10 Knee 93 (2003). Therapeutic interventions in this time period may be particularly important for opposing these catabolic processes and promoting cartilage repair.

IGF-1 Proteins and Functional Fragments and Variants Thereof

IGF-1 is the prototypical circulating factor that stimulates cartilage biosynthesis. Daughaday et al.,19 J. Clin. Endocrinol. Metab. 743 (1959); McQuillan et al., 240 Biochem. J. 423 (1986); Jones & Clemmons, 16 Endocrine Rev. 3 (1995). It also acts to oppose catabolic stimuli. Luyten et al., 267 Arch. Biochem. Biophys. 416 (1988); Tyler, 260 Biochem. J. 543 (1989). As a result, investigators have long sought to use IGF-1 as a therapy for cartilage repair. Trippel, 43 J. Rheumatol. Suppl. 129 (1995). Local delivery of IGF-1 and other growth factors is severely limited, however, by their short half-life in the joint. Investigators have developed options for gene therapy with IGF-1 and for IGF-1 encapsulated in hydrogels to allow for long-term controlled release to the joint cartilage. Although promising, these techniques have been slow to reach clinical trials. Evans et al., 7 Nat. Rev. Rheum. 244 (2011).

An example rat IGF-1 protein has the amino acid residues: GPETLCGAELVDALQFVCGPRGFYFNKPT-GYGSSIRRAPQTGIVDECCFRSCDLRRLEMYCAPLK PTKSA (SEQ ID NO:3). See, e.g., Tokunou et al., 22 FASEB J. 1886 (2008); see also Gene ID: 3489 (human IGF1). An example human IGF-1 has the amino acid residues: GPETLCGAELVDALQFVCGDRGFYFNKPT-GYGSSSRRAPQTGIVDECCFRSCDLRRLEMYCAPL KPAKSARSVRAQRHTDMPKTQKEVHLKNASRGSA (SEQ ID NO:4). Another example human IGF-1 (variant) has the amino acid residue sequence: GPETLCGAEL-VDALQFVCGDRGFYFNKPTGYGSSSRRAPQTGIV-DECCFRSCDLRRLEMYCAPL KPAKSA (SEQ ID NO:5). A variant of human IGF-1 that has biological activity (see WO 92/03477; GenBank: CAA01451.1) has the amino acid residues:
MEGPETLCGAELVDALQFVCGDRGFYFNKPT-GYGSSSRRAPQTGIVDECCFRSCDLRRL EMYCAPLK-PAKSA (SEQ ID NO:6).

It is known that truncation of the N-terminus of IGF-1 retains biological activity, e.g., the deletion of N-terminal amino acids GPE. Accordingly, in some embodiments, a human IGF-1 (variant) encompassed for use in the present invention has the amino acid residue sequence: TLCGAEL-VDALQFVCGDRGFYFNKPTGYGSSSRRAPQTGIV-DECCFRSCDLRRLEMYCAPLKPA KSA. (SEQ ID NO: 7).

Table 1 discloses examples of different embodiments of fusion of a HB peptide of SEQ ID NO: 1 or SEQ ID NO: 2 to variants of IGF-1 which are encompassed in the methods, kits and compositions as disclosed herein. The HB peptide of SEQ ID NO: 1 or SEQ ID NO: 2 (shown in bold) can be located at the 5' or 3' of IGF-1 variants.

TABLE 1

Examples of different embodiments of fusion of a HB peptide of SEQ ID NO: 1 or SEQ ID NO: 2 to variants of IGF-1

| HB peptide | IGF-1 variant | Sequence |
|---|---|---|
| C17S (SEQ ID NO: 1) | Rat-IGF-1 (SEQ ID NO: 3). | MKRKKKGKGLGKKRDPSLRKYKGPETLCGAE LVDALQFVCGPRGFYFNKPTGYGSSIRRAPQTGI VDECCFRSCDLRRLEMYCAPLKPTKSA (SEQ ID NO: 16). |
| C16S (SEQ ID NO: 2) | Rat-IGF-1 (SEQ ID NO: 3). | KRKKKGKGLGKKRDPSLRKYKGPETLCGAEL VDALQFVCGPRGFYFNKPTGYGSSIRRAPQTGIV DECCFRSCDLRRLEMYCAPLKPTKSA (SEQ ID NO: 17). |
| C17S (SEQ ID NO: 1) | Human IGF-1 (SEQ ID NO: 4). | MKRKKKGKGLGKKRDPSLRKYKGPETLCGAE LVDALQFVCGDRGFYFNKPTGYGSSSRRAPQTGI VDECCFRSCDLRRLEMYCAPLKPAKSARSVRAQ RHTDMPKTQKEVHLKNASRGSA (SEQ ID NO: 18). |
| C16S (SEQ ID NO: 2) | Human IGF-1 (SEQ ID NO: 4). | KRKKKGKGLGKKRDPSLRKYKGPETLCGAEL VDALQFVCGDRGFYFNKPTGYGSSSRRAPQTGIV DECCFRSCDLRRLEMYCAPLKPAKSARSVRAQR HTDMPKTQKEVHLKNASRGSA (SEQ ID NO: 19). |

TABLE 1-continued

Examples of different embodiments of fusion of a HB peptide of
SEQ ID NO: 1 or SEQ ID NO: 2 to variants of IGF-1

| HB peptide | IGF-1 variant | Sequence |
|---|---|---|
| C17S (SEQ ID NO: 1) | Human IGF-1 variant (SEQ ID NO: 5) | MKRKKKGKGLGKKRDPSLRKYKGPETLCGAEL VDALQFVCGDRGFYFNKPTGYGSSSRRAPQTGI VDECCFRSCDLRRLEMYCAPLKPAKSA (SEQ ID NO: 20) |
| C16S (SEQ ID NO: 2) | Human IGF-1 variant (SEQ ID NO: 5) | KRKKKGKGLGKKRDPSLRKYKGPETLCGAEL VDALQFVCGDRGFYFNKPTGYGSSSRRAPQTGIV DECCFRSCDLRRLEMYCAPLKPAKSA (SEQ ID NO: 21) |
| C17S (SEQ ID NO: 1) | Human IGF-1 variant (SEQ ID NO: 6) | MKRKKKGKGLGKKRDPSLRKYKMEGPETLC GAELVDALQFVCGDRGFYFNKPTGYGSSSRRAP QTGIVDECCFRSCDLRRLEMYCAPLKPAKSA (SEQ ID NO: 22). |
| C16S (SEQ ID NO: 2) | Human IGF-1 variant (SEQ ID NO: 6) | KRKKKGKGLGKKRDPSLRKYKMEGPETLCGA ELVDALQFVCGDRGFYFNKPTGYGSSSRRAPQT GIVDECCFRSCDLRRLEMYCAPLKPAKSA (SEQ ID NO: 23). |
| C17S (SEQ ID NO: 1) | Human IGF-1 variant (SEQ ID NO: 7) | MKRKKKGKGLGKKRDPSLRKYKTLCGAELV DALQFVCGDRGFYFNKPTGYGSSSRRAPQTGIVD ECCFRSCDLRRLEMYCAPLKPAKSA (SEQ ID NO: 24). |
| C16S (SEQ ID NO: 2) | Human IGF-1 variant (SEQ ID NO: 7) | KRKKKGKGLGKKRDPSLRKYKTLCGAELVDA LQFVCGDRGFYFNKPTGYGSSSRRAPQTGIVDEC CFRSCDLRRLEMYCAPLKPAKS (SEQ ID NO: 25). |
| C17S (SEQ ID NO: 1) | Rat-IGF-1 (SEQ ID NO: 3). | GPETLCGAELVDALQFVCGPRGFYFNKPTGYGSS IRRAPQTGIVDECCFRSCDLRRLEMYCAPLKPTK SAMKRKKKGKGLGKKRDPSLRKYK (SEQ ID NO: 26). |
| C16S (SEQ ID NO: 2) | Rat-IGF-1 (SEQ ID NO: 3). | GPETLCGAELVDALQFVCGPRGFYFNKPTGYGSS IRRAPQTGIVDECCFRSCDLRRLEMYCAPLKPTK SAKRKKKGKGLGKKRDPSLRKYK (SEQ ID NO: 27). |
| C17S (SEQ ID NO: 1) | Human IGF-1 (SEQ ID NO: 4). | GPETLCGAELVDALQFVCGDRGFYFNKPTGYGS SSRRAPQTGIVDECCFRSCDLRRLEMYCAPLKPA KSARSVRAQRHTDMPKTQKEVHLKNASRGSAM KRKKKGKGLGKKRDPSLRKYK (SEQ ID NO: 28). |
| C16S (SEQ ID NO: 2) | Human IGF-1 (SEQ ID NO: 4). | GPETLCGAELVDALQFVCGDRGFYFNKPTGYGS SSRRAPQTGIVDECCFRSCDLRRLEMYCAPLKPA KSARSVRAQRHTDMPKTQKEVHLKNASRGSAK RKKKGKGLGKKRDPSLRKYK (SEQ ID NO: 29). |
| C17S (SEQ ID NO: 1) | Human IGF-1 variant (SEQ ID NO: 5) | GPETLCGAELVDALQFVCGDRGFYFNKPTGYGS SSRRAPQTGIVDECCFRSCDLRRLEMYCAPLKPA KSAMKRKKKGKGLGKKRDPSLRKYK (SEQ ID NO: 30) |
| C16S (SEQ ID NO: 2) | Human IGF-1 variant (SEQ ID NO: 5) | GPETLCGAELVDALQFVCGDRGFYFNKPTGYGS SSRRAPQTGIVDECCFRSCDLRRLEMYCAPLKPA KSAKRKKKGKGLGKKRDPSLRKYK (SEQ ID NO: 31) |
| C17S (SEQ ID NO: 1) | Human IGF-1 variant (SEQ ID NO: 6) | MEGPETLCGAELVDALQFVCGDRGFYFNKPTGY GSSSRRAPQTGIVDECCFRSCDLRRLEMYCAPLK PAKSAMKRKKKGKGLGKKRDPSLRKYK (SEQ ID NO: 32). |
| C16S (SEQ ID NO: 2) | Human IGF-1 variant (SEQ ID NO: 6) | MEGPETLCGAELVDALQFVCGDRGFYFNKPTGY GSSSRRAPQTGIVDECCFRSCDLRRLEMYCAPLK PAKSAKRKKKGKGLGKKRDPSLRKYK (SEQ ID NO: 33). |

TABLE 1-continued

Examples of different embodiments of fusion of a HB peptide of SEQ ID NO: 1 or SEQ ID NO: 2 to variants of IGF-1

| HB peptide | IGF-1 variant | Sequence |
|---|---|---|
| C17S (SEQ ID NO: 1) | Human IGF-1 variant (SEQ ID NO: 7) | TLCGAELVDALQFVCGDRGFYFNKPTGYGSSSR RAPQTGIVDECCFRSCDLRRLEMYCAPLKPAKSA MKRKKKGKGLGKKRDPSLRKYK(SEQ ID NO: 34). |
| C16S (SEQ ID NO: 2) | Human IGF-1 variant (SEQ ID NO: 7) | TLCGAELVDALQFVCGDRGFYFNKPTGYGSSSR RAPQTGIVDECCFRSCDLRRLEMYCAPLKPAKSK RKKKGKGLGKKRDPSLRKYK (SEQ ID NO: 35). |

It is also encompassed that the HB peptide can be located at the N-terminus or C-terminus or at the N- and C-terminus of the IGF-1 protein or functional fragment or variant thereof. In some embodiments, the HB peptide can be located at the N-terminus or C-terminus or at the N- and C-terminus of the IGF-1 protein or functional fragment or variant thereof without a linker at each transition between the HB peptide and the IGF-1 protein or functional fragment or variant thereof. Accordingly, variations of the amino acid sequences in SEQ ID NO: 13 and 15 are encompassed where the HB is located at the C-terminus instead of the N-terminus. In additional embodiments, variations of the amino acid sequences of HB-IGF-1 fusion proteins (e.g., SEQ ID NO: 13 and 15) are encompassed where the HB is located at both the C- and N-terminus. Any combination of a HB peptide selected from SEQ ID NO: 1 or 2 can be used in any combination of a IGF-1 protein, where the HB peptide can be located at the N- and/or C-terminus of the IGF-1 protein or functional fragment or variant thereof.

Method of Treating Cartilage-Related Conditions and Disorders

The inventors have previously demonstrated an approach to stimulating cartilage biosynthesis uses an engineered rat IGF-1 protein fused with a rat heparin-binding domain, where the heparin-binding IGF-1 (HB-IGF-1) fusion protein is retained in cartilage after intra-articular injection. (Miller et al., 62 Arth. Rheum. 3686 (2010)). Herein, instead of the rat HB peptide used in Miller, the inventors have modified the wild type human HB construct, and surprisingly demonstrate that the HB constructs of SEQ ID NO: 1 or 2 as disclosed herein, where the C17 (on SEQ ID NO: 1) or C16 (on SEQ ID NO: 2) was changed from the wild-type residue of cysteine (C) to a serine (S), which results in significantly increased expression of the HB-IGF-1 fusion protein. The present specification thus demonstrates the kinetics of using HB-IGF-1 fusion protein comprising SEQ ID NO: 1 or SEQ ID NO: 2 after intra-articular injection, and shows functional stimulation of HB-IGF-1 on joint cartilage in vivo, and demonstrates therapeutic efficacy of HB-IGF-1 in vivo in a rat model of joint injury-induced arthritis. Accordingly, in some embodiments, a HB peptide of SEQ ID NO: 1 or 2 is fused to a IGF-1 protein or functional fragment thereof, e.g., any IGF-1 variant selected from the sequences from the group of: SEQ ID NO: 3-7 is encompassed for use in the present invention in methods to treat a cartilage-related disease or disorder.

Figure 3:
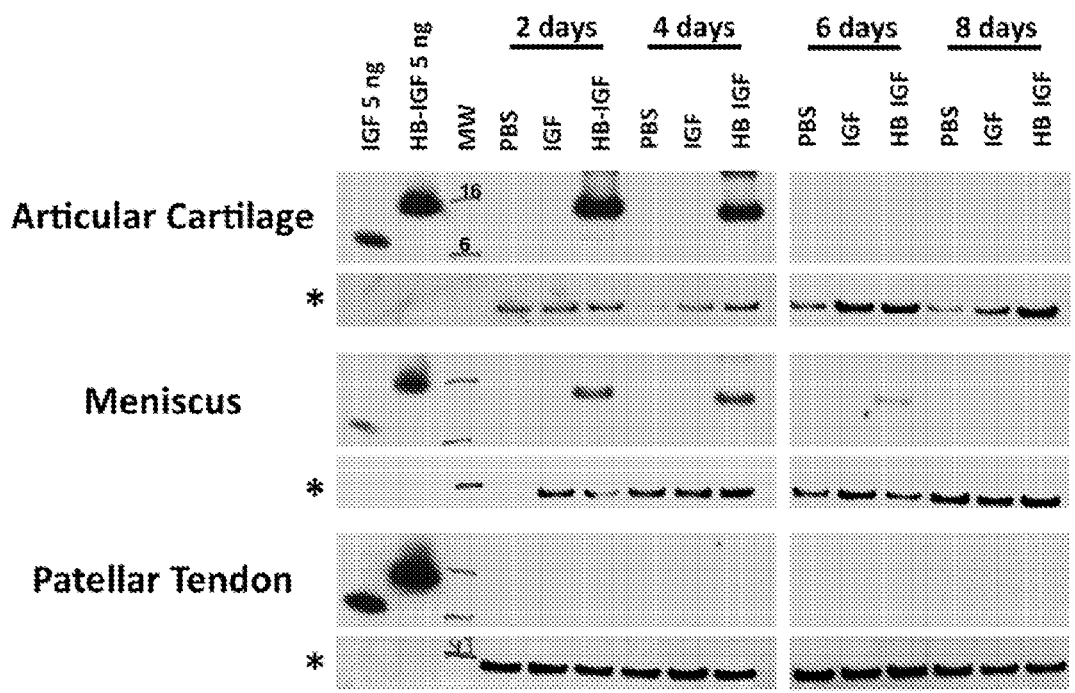
FIG. 3 provides data showing long term retention of an embodiment of HB-IGF-1 after intra-articular injection. Western blot analysis was performed for retained IGF-1 or HB-IGF-1 in rat articular cartilage, meniscus, or patellar tendon at 2, 4, 6, and 8 days after intra-articular injection of either IGF-1, HB-IGF-1, or PBS.
Figure 4:
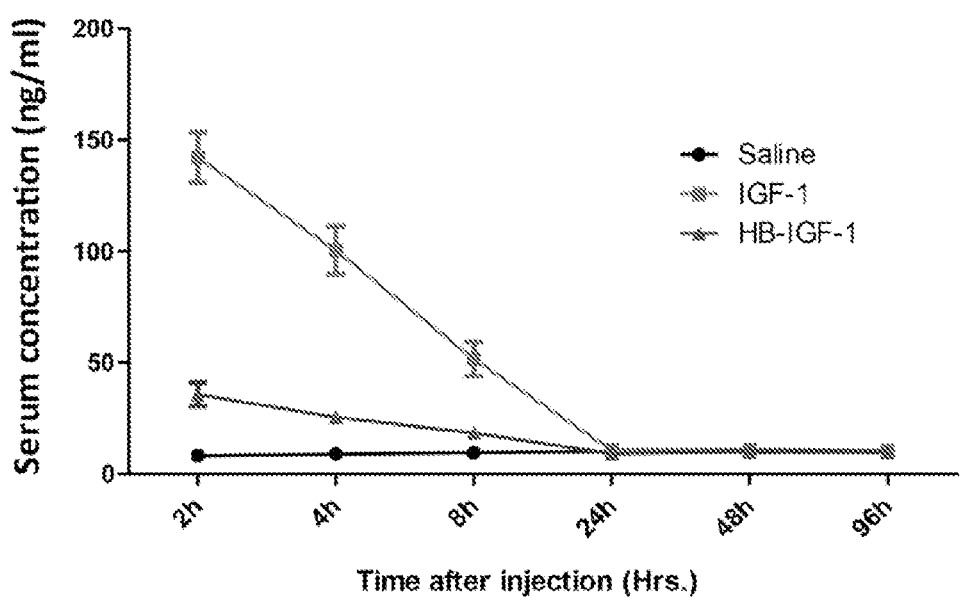
FIG. 4 shows serum levels of IGF-1 vs. HB-IGF-1 after intra-articular injection. Male Lewis rats 251-275 g (Charles River, Wilmington, Mass.) were randomly assigned to one of three groups (n=3 for each group) HB-IGF-1, IGF-1 or Saline. Rats received 50 µL intra-articular injections containing either 100 µg of HB-IGF-1, 100 µg IGF-1, or Saline in the right knee joint. Blood was harvested via tail vein at 2, 4, 8, 24, 48, and 96 hours after injection. Serum levels were measured with an ELISA (R&D Systems, Minneapolis, Minn.). HB-IGF-1 levels in serum were significantly lower than IGF-1 levels at the first three time points. HB-IGF-1 levels were not significantly different from Saline after 2 hours. This shows that intra-articular injection of HB-IGF-1 limits the amount of non-specific IGF-1 circulation compared with non-HB associated IGF-1.

The inventors demonstrate herein that, surprisingly, unlike IGF-1 alone (e.g., not fused to HB), a HB-IGF-1 fusion protein as disclosed herein is retained in cartilage after intra-articular injection. More specifically, to determine the kinetics of HB-IGF-1 binding to cartilage in vivo, joint tissues were harvested after injection and tissue extracts analyzed by Western analysis (FIG. 3). Two days after injection of IGF-1, there was no detectable IGF-1 remaining in any of the joint tissues harvested. In contrast, HB-IGF-1 was retained in both articular and meniscal cartilages, but not in patellar tendon. A similar result was observed four days after injection. By 6 to 8 days after injection, HB-IGF-1 was still detectable in the cartilage extracts but the immunoreactive bands were faint and more variable. These results demonstrate that, unlike IGF-1, the present HB-IGF-1 fusion protein is retained in articular cartilage for up to 8 days after intra-articular injection. The pharmacokinetics of IGF-1 in serum are shown in FIG. 4, indicating that intra-articularly injected HB-IGF-1 had markedly reduced leakage into the systemic circulation compared with unmodified IGF-1.

Figure 5:
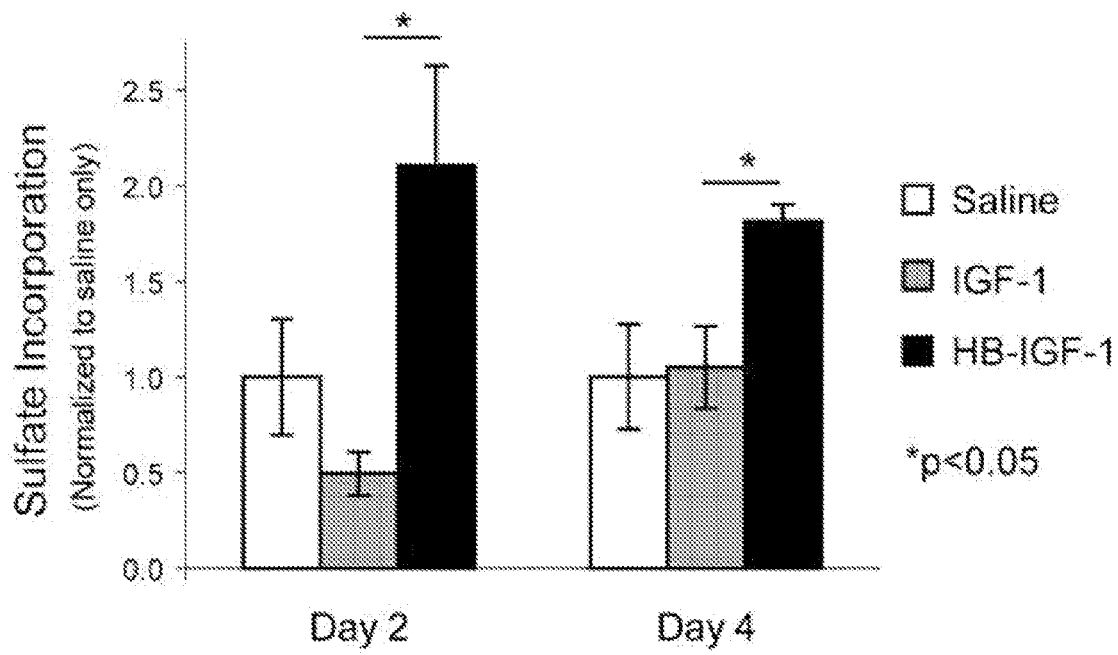
FIG. 5 is a bar graph depicting ex vivo sustained stimulation of cartilage biosynthesis and proliferation by HB-IGF-1 after intra-articular injection in rats. Rats received a single 50 µL intra-articular injection containing either 100 µg of an embodiment of HB-IGF-1, 100 µg IGF-1, or PBS in the right knee joint. Rats were sacrificed 2 and 4 days after the injection and the meniscus was harvested and cultured with radiolabel. Graph represents [$^{35}$S] sulfate incorporation in the meniscus 2 and 4 days after intra-articular injection. Results are shown as mean±SEM.

Additionally, the HB-IGF-1 produced sustained stimulation of cartilage biosynthesis in vivo. HB-IGF-1 remains able to activate cellular IGF-1 receptors in vivo despite its increased binding to chondroitin sulfate in the cartilage extracellular matrix. Sulfate incorporation into meniscal cartilage harvested after injection was measured and normalized to incorporation after injection of saline only (FIG. 5). Two days after injection, HB-IGF-1 stimulated a significantly higher rate of sulfate incorporation than did IGF-1 (HB-IGF: 2.10±0.52; IGF: 0.49±0.11; N=4-5/group; P=0.032). Four days after injection, sulfate incorporation remained significantly higher in the HB-IGF-1 group than in the IGF-1 group (HB-IGF: 1.82±0.09; IGF: 1.05±0.21; N=5/group; P=0.011).

Figure 6:
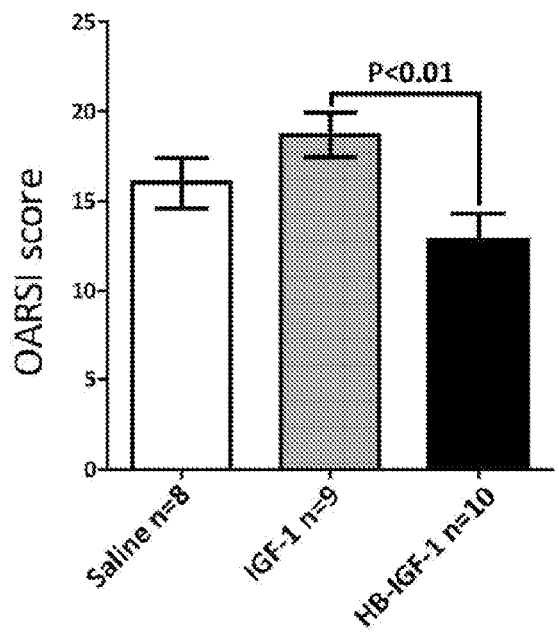
FIG. 6 is a bar graph from an osteoarthritis study comparing OARSI scores of HB-IGF-1, IGF-1, and PBS.

Further, HB-IGF-1 protects cartilage in vivo after transection of the medial meniscus. More specifically, HB-IGF-1 is efficacious in a rat model of surgically induced OA. Rats were subjected to medial meniscal tear (MMT) surgery and injected weekly with HB-IGF, IGF, or saline. Three weeks after MMT surgery, histological assessment of knee osteoarthritis (OA) was performed. For the primary outcome measure (FIG. 6), the overall OARSI score was significantly lower in the joints of the animals treated with HB-IGF-1 compared to control animals treated with IGF-1 (HB-IGF: 12.9±1.5; IGF: 18.7±1.2; N=9-10/group; P=0.008). Significant differences between HB-IGF-1 and IGF-1 treated knees were also observed on secondary analyses of total degeneration width and full-thickness cartilage loss, as shown in Table 2:

TABLE 2

Cartilage analysis in rat MMT model
(Results are shown as mean ± SEM).

|  | Saline (n = 8) | IGF-1 (n = 9) | HB-IGF-1 (n = 10) |
|---|---|---|---|
| Surface cartilage loss | 174 ± 56 | 207 ± 39 | 120 ± 41 |
| Full-thickness cartilage loss | 36 ± 15 | 95 ± 35 | 0 ± 0 |
| Total degeneration width | 436 ± 28 | 506 ± 57 | 343 ± 36 |
| Significant degeneration width | 202 ± 13 | 236 ± 30 | 178 ± 17 |

In some embodiments, the compositions as disclosed herein provide for a HB-IGF-1 therapeutic fusion protein that allows delivery and selective retention of bioactive proteins at a desired cite. HB-IGF-1 was retained in articular cartilage and meniscus 4 to 8 days after injection at levels sufficient to stimulate proteoglycan synthesis. IGF-1 alone (i.e., not fused to HB) was not so retained. Accordingly, local delivery of HB-IGF-1 in vivo can reduce disease progression in a rat meniscal tear model of arthritis. Compared with IGF-1 or vehicle, HB-IGF-1 significantly reduced progression of cartilage damage as measured by a modified OARSI score. Secondary analyses demonstrated a lower cartilage degeneration score and the prevention of full-depth cartilage loss, suggesting a global beneficial effect on cartilage.

Although IGF-1 is one of the major anabolic growth factors for cartilage, attempts to repair cartilage and prevent osteoarthritis (OA) with intra-articular injection of IGF-1 alone have not been successful (Rogachefsky et al., 1993; Schmidt et al., 2006). The present data demonstrate that these negative results were not due to lack of effect of IGF-1 itself, but likely rather because "free" IGF-1 is not retained in cartilage for a significant amount of time (IGF-1 was retained less than 24 hours) after intra-articular delivery.

Additionally, these data have implications for injectable protein therapies for cartilage in general. Development of future therapies should assess whether a targeting mechanism will be required to produce sustained delivery to chondrocytes. The kinetics of retention in cartilage can be verified in other models or experiments so that a negative experimental results of a particular agent is not interpreted as a failure of the agent itself. Interestingly, FGF-18, another growth factor that has been shown to be therapeutic in this model, is a heparin-binding growth factor (Moore et al., 2005, Hu et al., 1998; Chuang et al., 2010).

Further, the systemic pharmacokinetic data suggest that IGF-1 levels were not high enough to change glucose levels through binding to insulin receptors. If the increase in systemic levels is limited to ~24 hours, concerns about long-term elevation in IGF-1 levels will be abated.

Moreover, an unexpected result observed herein was the robust response of both articular and meniscal cartilage to HB-IGF-1. Although the charge density of meniscus is heterogeneous and lower than that of articular cartilage, HB-IGF-1 was retained at levels sufficient to stimulate proteoglycan synthesis in meniscus. This demonstrates that HB-IGF-1 fusion protein may be directly protective for both articular cartilage and meniscus, and thus may be particularly effective after meniscal injuries.

A HB-IGF-1 fusion protein may be less effective in late-stage OA as compared to early OA, because HB-IGF-1 may require the presence of sulfated proteoglycans in the matrix for long-term retention in the cartilage. However, in some embodiments, a HB-IGF-1 fusion protein can, on the other hand, can be used as an effective chondroprotective therapy (e.g., as a prophylactic treatment) in the setting of acute traumatic joint injury to a previously healthy joint.

The methods described herein may be used on cells, e.g., human cells, in vitro or ex vivo. Alternatively, the method can be performed on cells present in a subject as part of an in vivo (e.g., therapeutic or prophylactic) protocol. For example, the method can be used to treat or prevent a IGF-1-mediated indication in a subject, such as therapy for cartilage regeneration following injury. Accordingly, the invention provides a method of treating (e.g., curing, suppressing, ameliorating, delaying or preventing the onset of, or preventing recurrence or relapse of) or preventing permanent cartilage loss. The method includes administering to a subject a HB-IGF-1 fusion protein composition in an amount sufficient to inhibit or reduce cartilage loss or increase cartilage regeneration, thereby treating or preventing joint degeneration in a subject.

Accordingly, one aspect of the present invention relates to a method of treating a cartilage-related condition (e.g., damage or disease) comprising administering to a subject an effective amount of a HB-IGF-1 fusion protein as disclosed herein. In some embodiments, a HB-IGF-1 fusion protein as disclosed herein for the treatment of a cartilage-related condition can comprise at least one therapeutic protein, e.g., one selected from any protein or functional fragment thereof selected from the group of: IGF-1 or variants or functional fragments thereof (SEQ ID NO: 3-7).

Another aspect of the present invention relates to a method of treating a cartilage-related condition (e.g., damage or disease) comprising administering to a subject an amount of a HB-IGF-1 fusion protein as disclosed herein; and further administering concurrently or separately a Corticosteroid.

In some embodiments, a cartilage-related condition is a articular cartilage defect including rupture or detachment, a meniscal defect including a partial or complete tear, Osteoarthritis, Traumatic cartilage rupture or detachment, disease or damage to the meniscus and/or patella, Ankylosing spondylitis, Capsulitis, Psoriatic arthritis, Rheumatoid arthritis, Systemic lupus erythematosus, Juvenile idiopathic arthritis, or X-linked hypophosphatemic rickets.

In some embodiments, a cartilage-related condition is a rupture or detachment of the cartilage, a meniscal defect including a partial or complete tear or damage or a disease effecting the meniscus and/or patella. In some embodiments, a cartilage-related condition is selected from any or a combination of diseases from the following group: osteoarthritis (referred to herein as "OA" which results from breakdown of cartilage), including knee, finger, wrist, hip, ankle, elbow, toe, shoulder, and spinal osteoarthritis, traumatic cartilage rupture or detachment, ankylosing spondylitis, capsulitis, psoriatic arthritis, rheumatoid arthritis (RA), systemic lupus erythematosus, juvenile idiopathic arthritis, Chondropathy, Chondrosarcoma, Chondromalacia, Polychondritis, Relapsing Polychondritis, Slipped epiphysis, Osteochondritis Dissecans, Chondrodysplasia, Costochondritis, X-linked hypophosphatemic rickets, Osteochondroma, Chondrosarcoma (malignant), Osteoarthritis Susceptibility (types 1-6), Spondylosis, Osteochondroses, Primary chondrosarcoma, Chondrodysplasia, Tietze syndrome, Dermochondrocorneal dystrophy of Francois, Epiphyseal dysplasia, multiple, (types 1-5), Ossified Ear cartilages with Mental deficiency, Muscle Wasting and Bony Changes, Carpotarsal osteochondromatosis, Achondroplasia, Chondrocalcinosis (types 1-2), Genochondromatosis, Chondrodysplasia (disorder of sex development), Chondroma, Achondrogenesis (types 1A, 1B, 2, 3, 4, Langer-Saldino Type), Type II Achondrogenesis-Hypochondrogenesis, Atelosteogenesis, (type 1, 2 and III), Pyknoachondrogenesis, Pseudoachondroplasia, Osteoarthropathy of fingers, familial, Diastrophic dysplasia, Dyschondrosteosis-nephritis, Coloboma of Alar-nasal cartilages with telecanthus, Alar cartilages hypoplasia—coloboma-telecanthus, Pierre Robin syndrome—fetal chondrodysplasia, Dysspondyloenchondromatosis, Achondroplasia regional—dysplasia abdominal muscle, Osteochondritis Dissecans, Familial Articular Chondrocalcinosis, Tracheobronchomalacia, Chondritis, Dyschondrosteosis, Maffucci Syndrome, Jequier-Kozlowski-skeletal dysplasia, Chondrodystrophy, Cranio osteoarthropathy, Tietze's syndrome, Hip dysplasia—enchondromata-enchondromata, Bessel-Hagen disease, Chondromatosis (benign), Enchondromatosis (benign), chondrocalcinosis due to apatite crystal deposition, Meyenburg-Altherr-Uehlinger syndrome, Enchondromatosis-dwarfism-deafness, Astley-Kendall syndrome, Synovial osteochondromatosis, Chondrocalcinosis familial articular, Severe achondroplasia with developmental delay and acanthosis nigricans, Chondrocalcinosis, Keutel syndrome, Stanescu syndrome, Fibrochondrogenesis, Hypochondroplasia.

A subject amenable for the treatment with a HB-IGF-1 fusion protein as disclosed herein for the treatment of a cartilage-related condition is selected from a subject who has one or more symptoms of a joint disorder or cartilage loss or damage, including one or more symptoms from the group of: joint swelling, joint pain, joint redness, joint laxity, mild arthritis symptoms, haemorrhagic joint effusion, inflammatory joint effusion, joint hypermobility, non inflammatory joint effusion or other types.

In some embodiments, a subject is selected for administration of a composition comprising a HB-IGF-1 fusion protein as disclosed herein for the treatment of a cartilage-related condition is a subject who has familial osteochondritis dissecans, where the subject has a mutation of the ACAN gene. The ACAN gene provides instructions for making the aggrecan protein, which is a component of cartilage. Aggrecan attaches to the other components of cartilage, organizing the network of molecules that gives cartilage its strength. In addition, aggrecan attracts water molecules and gives cartilage its gel-like structure. This feature enables the cartilage to resist compression, protecting bones and joints. The ACAN gene mutation associated with familial osteochondritis dissecans results in an abnormal protein that is unable to attach to the other components of cartilage. As a result, the cartilage is abnormal and disorganized and weak and leads to the lesions and osteoarthritis characteristic of familial osteochondritis dissecans.

In some embodiments, a subject is selected for administration of a composition comprising a HB-IGF-1 fusion protein as disclosed herein for the treatment of a cartilage-related condition has an osteopenic related disease or osteoporosis, e.g., associated with the peri and post menopausal conditions. Also encompassed are the treatment and prophylaxis of Paget's disease, hypercalcemia associated with bone neoplasms and all the types of osteoporotic diseases as classified below according to their etiology: Primary osteoporosis, hypercalcemia, involutional osteoporosis, Type I or postmenopausal osteoporosis, Type II or senile osteoporosis, Juvenile osteoporosis, Idiopathic in young adults osteoporosis, Secondary osteoporosis, Endocrine abnormality, Hyperthyroidism, Hypogonadism, Ovarian agenesis, or Turner's syndrome, Hyperadrenocorticism or Cushing's syndrome, Hyperparathyroidism, Bone marrow abnormalities, Multiple myeloma and related disorders, and Systemic mastocytosis, disseminated carcinoma osteoporosis, Gaucher's disease, Connective tissue abnormalities, Osteogenesis imperfecta, Homocystinuria, Ehlers-Danlos syndrome, Marfan's syndrome, Menke's syndrome, Miscellaneous causes Immobilisation or weightlessness, Sudeck's atrophy, chronic obstructive pulmonary disease, chronic alcoholism, chronic heparin administration and chronic ingestion of anticonvulsant drugs Patients amenable to treatment with a composition comprising a HB-IGF-1 fusion protein as disclosed herein for the treatment of a cartilage-related condition as disclosed herein include patients at risk of disease but not showing symptoms (for example asymptomatic patients), as well as patients presently showing symptoms. In the case of OA or osteoporosis, virtually anyone, particularly women are at risk of suffering from OA and osteoporosis if he or she lives long enough.

In some embodiments, a subject is selected for administration of a composition comprising a HB-IGF-1 fusion protein as disclosed herein for the treatment of a cartilage-related condition is a subject known to have a genetic risk of a cartilage-related disease or disorder, e.g., OA. In some embodiments, patients are women, for example post menopausal, or women at least 65 years of age, or patients who have had previous fractures or have relatives who have had a metabolic bone disease, for example osteoporosis. Patients can be identified as having increased risk of developing metabolic bone disease using methods commonly known by person of ordinary skill in the art.

In some embodiments, a subject is selected for administration of a composition comprising a HB-IGF-1 fusion protein as disclosed herein for the treatment of a cartilage-related condition has at least one of the following conditions; rheumatoid arthritis (RA), Juvenile Rheumatoid Arthritis (JRA), psoriatic arthritis, Reiter's syndrome (reactive arthritis), Crohn's disease, ulcerative colitis and sarcoidosis (Orcel, et al., Bone demineralization and cytokines; Rev Rhum Mal Osteoartic.1992; 59:16S-22S; Brown, et al., The radiology of rheumatoid arthritis. Am Fam Physician. 1995. 52:1372-80; De Vos, et al., Bone and joint diseases in inflammatory bowel disease. Aliment Pharmacol Ther. 1998;12(5):397-404; Falcini, et al., The primary role of steroids on the osteoporosis in juvenile rheumatoid patients evaluated by dual energy X-ray absorptiometry. J Endocrinol Invest. 1996;19(3):165-9; Scutellari, et al., Rheumatoid arthritis: sequences. Eur J Radiol. 1998: Suppl 1:S31-8).

Rheumatoid arthritis is associated with a decrease in bone mass (Cortet, et al., Evaluation of bone mineral density in patients with rheumatoid arthritis. Influence of disease activity and glucocorticoid therapy. Rev Rhum Engl Ed. 1997 Jul.-Sep. 30, 1997; 64(7-9):451-8). Typical changes of an inflammatory arthritis include juxta-articular osteoporosis, cartilage loss, and cortical or marginal bone erosions (Lawson, et al., Lyme arthritis: radiologic findings. Radiology. 1985;154(1):37-43; Grassi, et al., The clinical features of rheumatoid arthritis. Eur J Radiol. 1998;1:S18-24).

In some embodiments, a subject is selected for administration of a composition comprising a HB-IGF-1 fusion protein as disclosed herein for the treatment of a cartilage-related condition who has a chronic inflammatory joint disease, such as rheumatoid arthritis, synovial cells produce large amounts of cytokines leading to increased local bone resorption and juxta-articular bone destructions (Orcel, P et al., Bone demineralization and cytokines. Rev Rhum Mal Osteoartic. 1992; 59(6 Pt 2):165-225).

Administration of Pharmaceutical Compositions

An effective amount, e.g., a therapeutically effective dose of an HB-IGF-1 fusion protein as disclosed herein may be administered to the patient in a single dose or in multiple doses. When multiple doses are administered, the doses may be separated from one another by, for example, one hour, three hours, six hours, eight hours, one day, two days, one week, two weeks, or one month. For example, a composition comprising HB-IGF-1 fusion protein as disclosed herein can be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, an effective amounts of a HB-IGF-1 fusion protein as disclosed herein can provided at a dose of 0.0001, 0.01, 0.01 0.1, 1, 5, 10, 25, 50, 100, 500, or 1,000 mg/kg. Effective doses may be extrapolated from dose-response curves derived from in vitro or animal model test bioassays or systems. Effective doses may be assessed using an in vivo in a rat model after transection of the medial meniscus (e.g., medial meniscal tear (MMT) surgery) as disclosed herein in the Examples, which is a rat model of surgically induced OA. After injection of the HB-IGF-1, histological assessment of knee osteoarthritis (OA) is performed and overall OARSI score is determined for the joints of the animals treated with the HB-IGF-1 is compared to control treated animals (e.g., IGF-1 alone).

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the IGF-1 protein or functional fragment or variant thereof, and the condition of the patient, the disease to be treated, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising a HB-IGF-1 fusion protein as disclosed herein are optionally tested in one or more appropriate in vitro and/or in vivo animal models of disease, such a cartilage assay as disclosed herein, or other models commonly known to persons of ordinary skill in the art, to confirm efficacy, tissue metabolism, and retention in the tissue over time, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of HB-IGF-1 at various concentrations, e.g., as applied to the mass and overall health of the patient. Administration can be accomplished via single or divided doses.

In determining the effective amount of a HB-IGF-1 fusion protein as disclosed herein to be administered in the treatment or prophylaxis of a disease, the physician can evaluate circulating plasma levels, formulation toxicities, and progression of the disease. The selected dosage level will also depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

In some embodiments, a HB-IGF-1 fusion protein as disclosed herein can be administered at a dose in accordance with good medical practice, taking into account the clinical condition of the individual patient, the site and method of administration, scheduling of administration, patient age, sex, body weight and other factors known to medical practitioners.

Dosage regimens of a composition comprising a HB-IGF-1 fusion protein as disclosed herein an be adjusted to provide the optimum desired response (e.g. a therapeutic or prophylactic response). For example, a single bolus can be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage.

Furthermore, actual dosage levels of a HB-IGF-1 fusion protein as disclosed herein in a pharmaceutical composition can be varied so as to obtain an amount of the active ingredient which is effective to achieve the desired therapeutic response for a particular subject, composition, and mode of administration, without being toxic to the subject. A pharmaceutical composition comprising a HB-IGF-1 fusion protein as disclosed herein as disclosed herein can be a "therapeutically effective amount" and/or a "prophylactically effective amount". In general, a suitable daily dose of a composition comprising a HB-IGF-1 fusion protein as disclosed herein will be that amount of the active agent X which is the lowest dose effective to produce a therapeutic effect, such as a reduction of a symptom of a disease for which the HB-IGF-1 fusion protein is being administered for. Such an effective dose will generally depend upon the factors described above.

If desired, the effective daily dose of a composition comprising a HB-IGF-1 fusion protein as disclosed herein can be administered as two, three, four, five, six or more sub-doses administered separately at appropriate intervals throughout the day, optionally, in unit dosage forms.

It is to be noted that dosage values may vary with the type and severity of the disease to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

For example, a therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is dependent of the desired therapeutic effect. For example, the therapeutically effective amount of a HB-IGF-1 fusion protein as disclosed herein for the treatment of a cartilage-related disease or disorder one can be assess the effect of the HB-IGF-1 fusion protein as disclosed herein in an in vivo in a rat model after transection of the medial meniscus (e.g., medial meniscal tear (MMT) surgery) as disclosed herein in the Examples, which is a rat model of surgically induced OA. After injection of the HB-IGF-1, histological assessment of knee osteoarthritis (OA) is performed and overall OARSI score is determined for the joints of the animals treated with the HB-IGF-1 is compared to control treated animals (e.g., IGF-1 alone), as described herein in the Examples.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. It is also noted that humans are treated generally longer than the mice or other experimental animals exemplified herein, which treatment has a length proportional to the length of the disease process and drug effectiveness. The doses may be single doses or multiple doses over a period of several days, but single doses are preferred.

In some embodiments, a HB-IGF-1 fusion protein as disclosed herein can be administered to humans and other animals for therapy by any suitable route of administration, including orally, nasally, as by, for example, a spray, rectally, intravaginally, by intra-articular injection, parenterally, intracisternally and topically, as by powders, ointments or drops, including buccally and sublingually.

An HB-IGF-1 fusion protein as disclosed herein can be administered by any route known in the art or described herein, for example, oral, parenteral (e.g., intravenously or intramuscularly), intraperitoneal, rectal, cutaneous, nasal, vaginal, inhalant, skin (patch), or ocular. The HB-IGF-1 fusion protein as disclosed herein may be administered in any dose or dosing regimen.

In some embodiments, a HB-IGF-1 fusion protein as disclosed herein can be administered to a subject as part of a biological implant or transplant. In some embodiments, a biological implant or transplant is incubated with a HB-IGF-1 fusion protein as disclosed herein as disclosed herein for a period of time prior to implanting the implant or transplant into the subject. Any biological implant known to one of ordinary skill in the art are encompassed for use herein, for example, but not limited to, osteochondral or meniscal allografts. In some embodiments, a biological scaffold is incubated with a HB-IGF-1 fusion protein as disclosed herein as disclosed herein for a period of time prior to implanting the scaffold into the subject. In some embodiments, the scaffold is a biocompatible and/or biodegradable scaffold.

In some embodiments, a HB-IGF-1 fusion protein as disclosed herein is administered to the subject in a hydrogel composition. Any biologically compatible hydrogel composition can be used, e.g., for example, but not limited to, a hydrogel comprising self-assembling peptides.

When the agents or compounds are delivered to a subject, they can be administered by any suitable route, including, for example, orally (e.g., in capsules, suspensions or tablets) or by parenteral administration. Parenteral administration can include, for example, intra-muscular, intravenous, intra-articular, intra-arterial, intrathecal, subcutaneous, or intra-peritoneal administration. The agent can also be administered orally, transdermally, topically, by inhalation (e.g., intra-bronchial, intranasal, oral inhalation or intranasal drops) or rectally. Administration can be local or systemic as indicated. Agents can also be delivered using viral vectors, which are well-known to those skilled in the art. The pharmaceutically acceptable formulations can be suspended in aqueous vehicles and introduced through conventional hypodermic needles or using infusion pumps.

Both local and systemic administration of a HB-IGF-1 fusion protein as disclosed herein are contemplated by the invention. Desirable features of local administration include achieving effective local concentrations of the active compound as well as avoiding adverse side effects from systemic administration of the active compound. Localized delivery techniques are described in, for example, 51 J. Biomed. Mat. Res. 96 (2000); 100 J. Control Release 211 (2004); 103 J. Control Release 541 (2005); 15 Vet. Clin. North Am. Equine Pract. 603 (1999); 1 Semin. Interv. Cardiol. 17 (1996).

The amount of agent administered to the individual will depend on the characteristics of the individual, such as general health, age, sex, body weight and tolerance to drugs as well as the degree, severity and type of disease as indicated. The skilled artisan will be able to determine appropriate dosages depending on these and other factors.

Accordingly, with respect to the therapeutic methods of the invention, it is not intended that the administration of a HB-IGF-1 fusion protein as disclosed herein be limited to a particular mode of administration, dosage, or frequency of dosing; the present invention contemplates all modes of administration, including intramuscular, intravenous, intraperitoneal, intravesicular, intra-articular, intralesional, subcutaneous, or any other route sufficient to provide a dose adequate to treat an disease or disorder as disclosed herein.

After formulation with an appropriate pharmaceutically acceptable carrier in a desired dosage, a pharmaceutical composition comprising a HB-IGF-1 fusion protein as disclosed herein can be administered to a subject. A pharmaceutical a composition comprising a HB-IGF-1 fusion protein as disclosed herein can be administered to a subject using any suitable means. In general, suitable means of administration include, but are not limited to, topical, oral, parenteral (e.g., intravenous, subcutaneous or intramuscular), rectal, intra-articular, intracisternal, intravaginal, intraperitoneal, ocular, or nasal routes.

In a specific embodiment, it may be desirable to administer the pharmaceutical composition comprising a HB-IGF-1 fusion protein as disclosed herein locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes. In some embodiments, a HB-IGF-1 fusion protein as disclosed herein are applied to the muscle using topical creams, patches, intramuscular injections and the like.

In some embodiments, a HB-IGF-1 fusion protein as disclosed herein can be administered to a subject orally (e.g., in capsules, suspensions or tablets) or by parenteral administration. Conventional methods for oral administration include administering a HB-IGF-1 fusion protein as disclosed herein as a tablets, suspensions, solutions, emulsions, capsules, powders, syrups and the like are usable. Known techniques that deliver a HB-IGF-1 fusion protein orally or intravenously and retain the biological activity are preferred. Parenteral administration can include, for example, intramuscular, intravenous, intra-articular, intraarterial, intrathecal, subcutaneous, or intraperitoneal administration. HB-X can also be administered orally, transdermally, topically, by inhalation (e.g., intrabronchial, intranasal, oral inhalation or intranasal drops) or rectally. Administration can be local or systemic as indicated. Agents, e.g., nucleic acid agents which encode a HB-IGF-1 fusion protein as disclosed herein can also be delivered using a vector, e.g., a viral vector by methods which are well known to those skilled in the art.

When administering a composition comprising a HB-IGF-1 fusion protein as disclosed herein is administered parenterally, it will generally be formulated in a unit dosage injectable form (e.g., solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (e.g., glycerol, propylene glycol, liquid polyethylene glycol), suitable mixtures thereof, and vegetable oils.

The term "Dosage unit" form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the HB-IGF-1 fusion protein as disclosed herein and the particular therapeutic or prophylactic effect to be achieved, and (b) the limitations inherent in the art of compounding a HB-IGF-1 fusion protein as an active for the treatment of sensitivity in individuals.

The pharmaceutically acceptable compositions comprising a HB-IGF-1 fusion protein as disclosed herein as disclosed herein can be suspended in aqueous vehicles and introduced through conventional hypodermic needles or using infusion pumps.

The methods described herein may be used to deliver a HB-IGF-1 fusion protein to cells, e.g., human cells, in vitro or ex vivo. Alternatively, the method of administering a HB-IGF-1 fusion protein as disclosed herein can be performed on cells present in a subject as part of an in vivo (e.g., therapeutic or prophylactic) protocol. For example, the method can be used to treat or prevent a IGF-1-mediated indication in a subject, such as therapy for cartilage regeneration following injury. Accordingly, the invention provides a method of treating (e.g., curing, suppressing, ameliorating, delaying or preventing the onset of, or preventing recurrence or relapse of) or preventing permanent cartilage loss. The method includes administering to a subject a HB-IGF-1 fusion proteins as disclosed herein in an amount sufficient to inhibit or reduce cartilage loss or increase cartilage regeneration, thereby treating or preventing joint degeneration in a subject.

Pharmaceutical Compositions

In some embodiments, a composition comprising a HB-IGF-1 fusion proteins as disclosed herein comprising SEQ ID NO: 1 or SEQ ID NO: 2 can be formulated in a pharmaceutically acceptable formulation known to persons of ordinary skill in the art. In some embodiments, a pharmaceutically acceptable formulation may include a pharmaceutically acceptable carrier(s) or excipient(s), solvents, dispersion media, coatings, antibacterial and antifungal agents, isotonic and absorption delaying agents, and the like, that are physiologically compatible. For example, the carrier can be suitable for intra-articular injection. Excipients include pharmaceutically acceptable stabilizers. The present invention pertains to any pharmaceutically acceptable formulations, including synthetic or natural polymers in the form of macromolecular complexes, nanocapsules, microspheres, or beads, and lipid-based formulations including oil-in-water emulsions, micelles, mixed micelles, synthetic membrane vesicles, and gels such as hyaluronic gels.

In some embodiments, a composition comprising a HB-IGF-1 fusion protein as disclosed herein can be formulated in any suitable means, e.g., as a sterile injectable solution, e.g., which can be prepared by incorporating the HB-IGF-1 fusion protein in the required amount of the appropriate solvent with various of the other ingredients, as desired.

In another embodiment of the invention, a composition comprising a HB-IGF-1 fusion protein as disclosed herein, can be administered and/or formulated in conjunction (e.g., in combination) with any other therapeutic agent. For purpose of administration, a HB-IGF-1 fusion protein as disclosed herein is preferably formulated as a pharmaceutical composition. Pharmaceutical compositions of the present invention comprise a compound of this invention and a pharmaceutically acceptable carrier, wherein the compound is present in the composition in an amount which is effective to treat the condition of interest. Appropriate concentrations and dosages can be readily determined by one skilled in the art.

Pharmaceutically acceptable carriers are familiar to those skilled in the art. For compositions formulated as liquid solutions, acceptable carriers include saline and sterile water, and may optionally include antioxidants, buffers, bacteriostats and other common additives.

The compositions of the present invention can be in any form. These forms include, but are not limited to, solutions, suspensions, dispersions, ointments (including oral ointments), creams, pastes, gels, powders (including tooth powders), toothpastes, lozenges, salve, chewing gum, mouth sprays, pastilles, sachets, mouthwashes, aerosols, tablets, capsules, transdermal patches.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Both local and systemic administration are contemplated by the invention. Desirable features of local administration include achieving effective local concentrations of the active compound as well as avoiding adverse side effects from systemic administration of the active compound. Localized delivery techniques are described in, for example, 51 J. Biomed. Mat. Res. 96 (2000); 100 J. Control Release 211 (2004); 103 J. Control Release 541 (2005); 15 Vet. Clin. North Am. Equine Pract. 603 (1999); 1 Semin. Interv. Cardiol. 17 (1996).

The amount of agent administered to the individual will depend on the characteristics of the individual, such as general health, age, sex, body weight and tolerance to drugs as well as the degree, severity and type of disease as indicated. The skilled artisan will be able to determine appropriate dosages depending on these and other factors.

Vectors:

In another embodiment, this invention provides vector encoding a HB-IGF-1 fusion protein as disclosed herein for use in the methods, compositions and kits as disclosed herein. In some embodiments, the present invention relates to a vector encoding the HB-IGF-1 fusion protein comprising a nucleic acid encoding at least one heparin binding peptide (HB) selected from MKRKKKGKGLGKKRDPSLRKYK (SEQ ID NO:1) or KRKKKGKGLGKKRDPSLRKYK (SEQ ID NO:2) and at least one nucleic acid sequence encoding a IGF-1 protein or functional fragment thereof as disclosed herein, e.g., SEQ ID NO: 3-7. In some embodiments, the present invention relates to a vector encoding a HB-IGF-1 fusion protein which comprises the nucleic acid sequence of SEQ ID NO: 12 or 14 as disclosed herein in the Examples.

In some embodiments, the vector encoding the HB-IGF-1 fusion protein comprises a nucleic acid sequence which encodes at least one HB-IGF-1 fusion protein, wherein HB is a heparin binding peptide selected from MKRKKKGKGLGKKRDPSLRKYK (SEQ ID NO:1) or KRKKKGKGLGKKRDPSLRKYK (SEQ ID NO:2), and IGF-1 is a protein of SEQ ID NO: 3-7 or a functional fragment or variant or derivative thereof, and n is an integer of at least 1.

Kits

In another embodiment, this invention provides kits for the practice of the methods of this invention. The kits preferably include one or more containers containing a HB-IGF-1 fusion protein as disclosed herein. In some embodiments, a kit can comprise a vector encoding the HB-IGF-1 fusion protein comprising a nucleic acid encoding at least one heparin binding peptide (HB) selected from MKRKKKGKGLGKKRDPSLRKYK (SEQ ID NO:1) or KRKKKGKGLGKKRDPSLRKYK (SEQ ID NO:2), and at least one IGF-1 protein or functional fragment or derivative thereof as disclosed herein, and suitable reagents for expressing the HB-IGF-1 fusion protein. In some embodiments, the kit comprises a vector comprising a nucleic acid sequence encoding a HB-IGF-1 fusion protein, where the vector comprises a nucleic acid encoding at least one heparin binding peptide (HB) selected from MKRKKKGKGLGKKRDPSLRKYK (SEQ ID NO:1) or KRKKKGKGLGKKRDPSLRKYK (SEQ ID NO:2) and at least one nucleic acid sequence encoding a IGF-1 protein or functional fragment thereof as disclosed herein, e.g., SEQ ID NO: 3-7.

Another embodiment, a kit may comprise a HB-IGF-1 fusion protein as disclosed herein for treatment of a disease or condition, e.g., a cartilage-related disease or disorder.

A kit may optionally contain additional therapeutics to be co-administered with the HB-IGF-1 fusion protein as disclosed herein. The kit may comprise instructions for administration of a HB-IGF-1 fusion protein as disclosed herein to a subject with a cartilage-related disease or disorder.

The kits may also optionally include appropriate systems (e.g. opaque containers) or stabilizers (e.g. antioxidants) to prevent degradation of the HB-IGF-1 fusion protein by light or other adverse conditions.

In another aspect of the invention provides kits including one or more containers containing a HB-IGF-1 fusion protein as disclosed herein and a pharmaceutically acceptable excipient. The kit may optionally contain additional therapeutics to be co-administered with the HB-IGF-1 fusion protein. The kit may comprise instructions for administration of a subject with a cartilage-related disease or disorder etc.

The kits may optionally include instructional materials containing directions (i.e., protocols) providing for the use of HB-IGF-1 fusion protein for the treatment of a disease in a mammal, e.g., for the treatment of a cartilage-related disease or disorder.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In Some Embodiments, the Present Invention may be Defined in Any of the Following Numbered Paragraphs 1. A composition comprising a HB-X fusion protein, wherein HB is a heparin binding peptide having the amino acid sequence (MKRKKKGKGLGKKRDPSLRKYK) (SEQ ID NO:1) or (KRKKKGKGLGKKRDPSLRKYK) (SEQ ID NO:2), and X is Insulin-like growth factor 1 (IGF 1), or functional portion, variant, analog, or derivative thereof.
2. The composition of any one of the preceding paragraphs, wherein the IGF-1 is a human IGF 1.
3. A method of treating cartilage-related clinical conditions (e.g., damage or disease) comprising administering to a subject an effective amount of a fusion protein of any one of the preceding paragraphs.
4. The method of paragraph 3, wherein the cartilage-related condition is a articular cartilage defect including rupture or detachment, a meniscal defect including a partial or complete tear, Osteoarthritis, Traumatic cartilage rupture or detachment, Ankylosing spondylitis, Capsulitis, Psoriatic arthritis, Rheumatoid arthritis, Systemic lupus erythematosus, Juvenile idiopathic arthritis, or X-linked hypophosphatemic rickets.
5. The composition of paragraph 1, wherein the IGF-1 comprises the amino acid sequence of SEQ ID NO: 4, 5, 6 or 7.
6. The composition of any of paragraphs 1 and 5, wherein the IGF-1 comprises the amino acid sequence of SEQ ID NO: 4, 5, 6 or 7.
7. The composition of any of paragraphs 1 and -6, wherein the HB is fused to the N-terminus of IGF-1.
8. The composition of any of paragraphs 1 and 5-7, wherein the HB is fused to the C-terminus of IGF-1.
9. The composition of any of paragraphs 1 and 5-8, wherein the HB is fused to the N- and the C-terminus of IGF-1.
10. The composition of any of paragraphs 1 and 5-9, wherein the HB-X fusion protein comprises amino acids of SEQ ID NO: 13 or SEQ ID NO: 15.

11. The composition of any of paragraphs 1, 3 and 5-9, for delivering IGF-1 or a functional portion, variant, analog, or derivative thereof to a cell or tissue expressing proteoglycans.
12. The composition of any of paragraphs 1 and 5-11, wherein the cell or tissue is cartilage tissue.
13. A vector comprising a nucleic acid construct encoding at least one HB peptide having the amino acid sequence selected from: MKRKKKGKGLGKKRDPSLRKYK) (SEQ ID NO:1) or (KRKKKGKGLGKKRDPSLRKYK) (SEQ ID NO:2), and at encoding least one Insulin-like growth factor 1 (IGF 1), or functional portion, variant, analog, or derivative thereof.
14. The vector of paragraph 13, wherein the nucleic acid construct encodes an IGF-1 protein with the amino acid sequence selected from SEQ ID NO: 4, 5, 6 or 7. is. The vector of any of paragraphs 13-14, wherein the vector comprises the nucleic acid sequence of SEQ ID NO: 12 or 14.
16. The vector of any of paragraphs 13-15, wherein the vector is an expression vector.
17. A kit comprising a HB-IGF-1 fusion protein and a pharmaceutically acceptable carrier, wherein the HB is a heparin binding peptide having the amino acid sequence (MKRKKKGKGLGKKRDPSLRKYK) (SEQ ID NO:1) or (KRKKKGKGLGKKRDPSLRKYK) (SEQ ID NO:2), and IGF-1 is an IGF-1 protein or functional portion, variant, analog, or derivative thereof.
18. A kit comprising the vector of any of paragraphs 13-16 and reagents for expression of the HB-IGF-1 fusion protein.
19. A cell line comprising a vector of any of paragraphs 13-16.

Embodiments will now be described further by non-limiting examples.

EXAMPLES

Example 1

Construction of HB-IGF-1 Fusion Protein

DNA was chemically synthesized (GenScript) to encode for various HB-IGF-1 constructs. The first construct used amino acid sequences derived from rat HB-EGF and rat IGF-1 (Rat "Wild-Type" HB-IGF-1). Others were derived from human HB-EGF and human IGF-1 and were optimized for *E. coli* expression by modifying the DNA to use preferred codons. The locations of mutations are shown in bold in the following sequences:

```
Rat "Wild-Type" HB-IGF-1: (nucleic acid)
                                                   (SEQ ID NO: 8)
ATGAAAAAG AAGAGGAAAGGC AAGGGGTTAGGA AAGAAGAGAGAT CCATGCCTTAAG
AAATACAAGGGA CCAGAGACCCTT TGCGGGGCTGAGCTGGTGGACGCT CTTCAATTCGTG
TGTGGACCAAGG GGCTTTTACTTCAACAAGCCCACA GGCTATGGCTCC AGCATTCGGAGG
GCACCACAGACGGGCATTGTGGAT GAGTGTTGCTTC CGGAGCTGTGAT
CTGAGGAGGCTGGAGATGTACTGT GCTCCGCTGAAG CCTACAAAGTCA GCTTAG Rat "Wild-Type" HB-IGF-1: (amino acid)
                                                   (SEQ ID NO: 9)
MetLysLys LysArgLysGly LysGlyLeuGly LysLysArgAsp ProCysLeuLys
LysTyrLysGly ProGluThrLeu CysGlyAlaGlu LeuValAspAla LeuGlnPheVal
CysGlyProArg GlyPheTyrPheAsnLysProThr GlyTyrGlySer SerIleArgArg
AlaProGlnThr GlyIleValAsp GluCysCysPhe ArgSerCysAsp LeuArgArgLeu
GluMetTyrCys AlaProLeuLys ProThrLysSer Ala "Wild-Type" HB-IGF-1: (nucleic acid)
                                                   (SEQ ID NO: 10)
ATGAAGCGT AAGAAAAAAGGC AAAGGTCTGGGCAAAAAACGTGATCCGTGCCTGCGC
AAATATAAAGGT CCGGAAACCCTG TGCGGCGCAGAACTGGTGGATGCG CTGCAGTTTGTT
TGTGGTGATCGT GGCTTTTATTTCAACAAACCGACC GGTTACGGTAGC TCTAGTCGTCGC
GCACCGCAGACGGGTATTGTGGAT GAATGCTGTTTC CGCAGCTGCGAT
CTGCGTCGCCTGGAAATGTACTGT GCGCCGCTGAAA CCGGCGAAATCT GCCTAATAA Wild-Type" HB-IGF-1 (amino acid)
                                                   (SEQ ID NO: 11)
MetLysArg LysLysLysGly LysGlyLeuGly LysLysArgAsp ProCysLeuArg
LysTyrLysGly ProGluThrLeu CysGlyAlaGlu LeuValAspAla LeuGlnPheVal
CysGlyAspArg GlyPheTyrPhe AsnLysProThr GlyTyrGlySer SerSerArgArg
AlaProGlnThr GlyIleValAsp GluCysCysPhe ArgSerCysAsp LeuArgArgLeu
GluMetTyrCys AlaProLeuLys ProAlaLysSer Ala HB-IGF-1 C17S (nucleic acid)
                                                   (SEQ ID NO: 12)
ATGAAGCGT AAGAAAAAAGGC AAAGGTCTGGGC AAAAAACGTGATCCGAGCCTGCGC
AAATATAAAGGT CCGGAAACCCTG TGCGGCGCAGAACTGGTGGATGCG CTGCAGTTTGTT
TGTGGTGATCGT GGCTTTTATTTCAACAAACCGACC GGTTACGGTAGC TCTAGTCGTCGC
GCACCGCAGACGGGTATTGTGGAT GAATGCTGTTTC CGCAGCTGCGAT
CTGCGTCGCCTGGAAATGTACTGT GCGCCGCTGAAA CCGGCGAAATCT GCCTAATAA HB-IGF-1 C17S (amino acid)
                                                   (SEQ ID NO: 13)
MetLysArg LysLysLysGly LysGlyLeuGly LysLysArgAspProSerLeuArg
LysTyrLysGly ProGluThrLeu CysGlyAlaGluLeuValAspAla LeuGlnPheVal
CysGlyAspArg GlyPheTyrPheAsnLysProThr GlyTyrGlySer SerSerArgArg
AlaProGlnThrGlyIleValAsp GluCysCysPhe ArgSerCysAsp LeuArgArgLeu
GluMetTyrCys AlaProLeuLys ProAlaLysSer Ala
```

-continued

HB-IGF-1 C17S M59N (nucleic acid)
(SEQ ID NO: 14)
ATGAAGCGT AAGAAAAAAGGC AAAGGTCTGGGC AAAAAACGTGATCCGAGCCTGCGC
AAATATAAAGGT CCGGAAACCCTG TGCGGCGCAGAACTGGTGGATGCG CTGCAGTTTGTT
TGTGGTGATCGT GGCTTTTATTTCAACAAACCGACC GGTTACGGTAGC TCTAGTCGTCGC
GCACCGCAGACGGGTATTGTGGAT GAATGCTGTTTC CGCAGCTGCGAT
CTGCGTCGCCTGGAAAACTACTGT GCGCCGCTGAAA CCGGCGAAATCT GCCTAATAA HB-IGF-1 C17S M59N (amino acid)
(SEQ ID NO: 15)
MetLysArg LysLysLysGly LysGlyLeuGly LysLysArgAspProSerLeuArg
LysTyrLysGly ProGluThrLeu CysGlyAlaGluLeuValAspAla LeuGlnPheVal
CysGlyAspArg GlyPheTyrPheAsnLysProThr GlyTyrGlySer SerSerArgArg
AlaProG\lnThrGlyIleValAsp GluCysCysPhe ArgSerCysAsp LeuArgArgLeu
GluAsnTyrCys AlaProLeuLys ProAlaLysSer Ala The "Wild-Type" HB-IGF-1 construct (e.g., SEQ ID NO: 10 and 11) had no mutations. The HB-IGF-1 C17S (SEQ ID NO: 12 and 13) and HB-IGF-1 C17S M59N (SEQ ID NO: 14 and 15) constructs both had the cysteine-to-serine mutation (C17S) and the HB-IGF-1 C17S M59N (SEQ ID NO: 14 and 15) construct also had the methionine-to-asparagine mutation (M59N).

All constructs were cloned into the expression plasmid pET24a (Novagen) using NdeI and EcoRI restriction sites and standard techniques. The resulting plasmids were then used to transform *E. coli* expression strain C2566 (New England Biolabs). Individual clones were selected and grown in rich medium at 37° C. and induced with 1 mM IPTG for 4 hr. The induced cells were then collected and normalized against their optical density. To obtain the HB-IGF-1 protein, whole cells were lysed using BugBuster (Novagen) and the lysate run under non-reducing conditions on SDS-PAGE using Novex 4-12% gradient gels, MES buffer and Novex Sharp Standards. The gels were then stained with Simply Blue stain (Novex), scanned and the relative expression levels determined by densitometry. All constructs were run in quadruplicate, and cells that were not induced and cells containing only the unmodified pET24a plasmid were used as negative controls.

Figure 2:
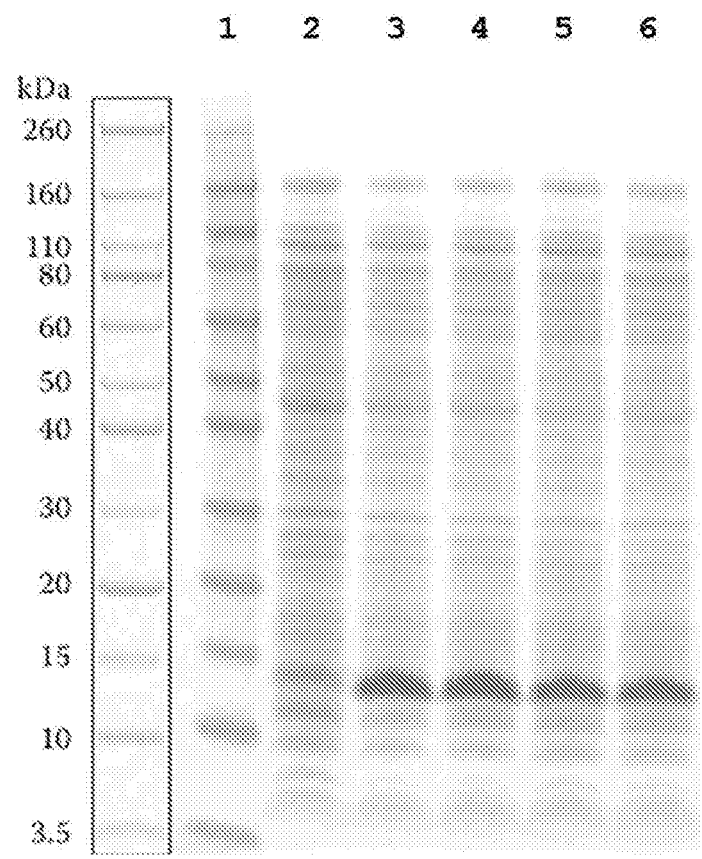
FIG. 2 shows a SDS-PAGE gel showing relative expression levels of mutant HB-IGF-1 constructs in *E. coli*. Lane 1, Novex Sharp Standard; lane 2, Uninduced pET24a; lanes 3-6, HB-IGF-1 C17S M59N.

Setting the HB-IGF-1 C17S construct expression-level to 100%, the rat "wild-type" HB-IGF-1, the "wild-type" HB-IGF-1 (FIG. 1) and HB-IGF-1 C17S M59N (FIG. 2) construct expression-levels were 6.1%, 20.3%, and 112%, respectively. The HB-IGF-1 protein constructs with the cysteine-to-serine mutations were better expressed than those containing the cysteine residue. Additionally, the methionine-to-asparagine mutation had little or no effect on protein expression.

Example 2

In Vivo Binding and Pharmacokinetics

Experiments were performed with male Lewis rats (251-275 g, Charles River, Wilmington, Mass.). All animal procedures were approved by the Harvard Medical Area Standing Committee on Animals. An HB-IGF-1 construct was made to express the heparin-binding domain of human HB-EGF, containing a single cysteine-to-serine mutation (MKRKKKGKGLGKKRDPSLRKYK) (SEQ ID NO:1), fused to the amino-terminus of a mature IGF-1 protein. HB-IGF-1 was produced by recombinant expression in *E. coli*, refolded, and purified by reverse-phase chromatography. Human recombinant IGF-1 is available commercially, for example Increlex® (mecasemin [rDNA origin], Ipsen Biopharmaceuticals, Inc., Basking Ridge, N.J.).

Rats received a single intraarticular injection containing 100 μg of HB-IGF-1, 100 μg IGF-1, or phosphate buffered saline (PBS) in the right patellofemoral joint. Articular cartilage, medial meniscus and patellar tendon samples were harvested at 2, 4, 6, and 8 days after injection. Samples were weighed, pulverized while in liquid nitrogen and extracted with 10 μl of lysis buffer (100 mM NaCl, 50 mM Tris, 0.5% Triton X-100, 5 mM EDTA, 1 mM PMSF, and protease inhibitor cocktail [Roche]) per milligram of tissue. Portions of extracts with equal protein mass were analyzed by Western blotting. Serum IGF-1 levels were measured by ELISA (R&D Systems #DY291) reactive with human but not rodent IGF-1.

Example 3

Cartilage Biosynthesis Assay

Rats were randomly assigned to receive a single intraarticular injection containing 100 μg of HB-IGF-1, 100 μg IGF-1, or PBS in the right patellofemoral joint. Animals were sacrificed either 2 or 4 days after injection. Following sacrifice, the meniscus from the right knee joint was harvested and incubated at 37° C. in Dulbecco's Modified Eagle Medium (DMEM) containing 5 μCi/ml $^{35}$S-sulfate for 18 hr. Following incubation, samples were washed four times for 15 min in PBS with sulfate to remove unincorporated radiolabel. Samples were digested overnight with 1 mg/ml Proteinase K at 60° C. and radiolabel incorporation was measured in a liquid scintillation counter.

Example 4

Rat Model of Joint Damage

For surgical procedures, rats were randomly assigned to one of three groups: 50 μL intraarticular injections containing 100 μg of HB-IGF-1, 100 μg IGF-1, or PBS in the right knee joint. Initial injections were administered 1 day prior to medial meniscal tear (MMT). The MMT model was used as previously described. Gerwin et al., 18 Osteoarthr. Cartil. S24 (2010). Briefly, a skin incision was made across the medial aspect of the knee. The medial collateral ligament was exposed by blunt dissection and transected. The medial meniscus was reflected medially and cut to simulate a full tear. Subsequent intraarticular injections were administered 7 and 14 days post MMT. Animals were sacrificed 21 days after surgery.

Histological staging and sectioning was performed. Knee joints were harvested and fixed in 4% paraformaldehyde. Joints were then transferred to 5% formic acid decalcifying solution (ImmunoCal, Decal Chemical Corp, Tallman, N.Y.). Joints were cut in half to form anterior and posterior sections, and embedded in paraffin. 8 μm sections taken approximately 200 μm apart were stained with Toluidine Blue.

The medial tibial plateau was analyzed and imaged microscopically. The central most sections exhibiting the maximum injury extent were selected for blinded scoring. Injuries were scored using a modified Mankin scoring system. Injuries were measured using three different metrics: cartilage matrix loss width, total cartilage degeneration width, and significant degeneration width.

Cartilage matrix loss width measured only the extent of 100% matrix loss while areas of PG or chondrocyte degeneration are ignored. Measurements were taken at the surface (0% depth) and at the tidemark (100%) depth. Total cartilage degeneration width measured the total width of the area of articular cartilage affected by any type of degenerative change. Significant cartilage degeneration width measured the extent of injury that affects more than 50% of the thickness of cartilage. Significant cartilage degeneration width included any form of collagen matrix, PG, or chondrocyte degeneration. All results are expressed as mean±SEM.

The invention claimed is:

1. A composition comprising a HB-X fusion protein, wherein HB is a heparin binding peptide having the amino acid sequence (MKRKKKGKGLGKKRDPSLRKYK) (SEQ ID NO:1) or (KRKKKGKGLGKKRDPSLRKYK) (SEQ ID NO:2), and X is Insulin-like growth factor 1 (IGF-1), and further wherein the IGF-1 is a human IGF-1.

2. A composition comprising a HB-X fusion protein, wherein HB is a heparin binding peptide having the amino acid sequence (MKRKKKGKGLGKKRDPSLRKYK) (SEQ ID NO:1) or (KRKKKGKGLGKKRDPSLRKYK) (SEQ ID NO:2), and Xis Insulin-like growth factor 1 (IGF-1), wherein the IGF-1 comprises the amino acid sequence of SEQ ID NO: 4, 5, 6 or 7.

3. A composition comprising a HB-X fusion protein, wherein HB is a heparin binding peptide having the amino acid sequence (MKRKKKGKGLGKKRDPSLRKYK) (SEQ ID NO:1) or (KRKKKGKGLGKKRDPSLRKYK) (SEQ ID NO:2), and Xis Insulin-like growth factor 1 (IGF-1), wherein the HB-X fusion protein comprises amino acids of SEQ ID NO: 13 or SEQ ID NO: 15.

* * * * *